(12) United States Patent
Stuessel et al.

(10) Patent No.: US 11,206,805 B2
(45) Date of Patent: Dec. 28, 2021

(54) AUTOMATED MILKING SYSTEM SAFETY VALVE ARRANGEMENT

(71) Applicant: GEA Farm Technologies GmbH, Bönen (DE)

(72) Inventors: Matthew J Stuessel, Alma Center, WI (US); Wolfgang Schulze-Wilmert, Gronau (DE); Thomas Orban, Dortmund (DE)

(73) Assignee: GEA Farm Technologies GmbH, Bönen (DE)

( * ) Notice: Subject to any disclaimer, the term of this patent is extended or adjusted under 35 U.S.C. 154(b) by 341 days.

(21) Appl. No.: 16/179,660

(22) Filed: Nov. 2, 2018

(65) Prior Publication Data

US 2019/0133067 A1  May 9, 2019

Related U.S. Application Data

(60) Provisional application No. 62/581,514, filed on Nov. 3, 2017, provisional application No. 62/581,526, filed on Nov. 3, 2017.

(51) Int. Cl.
| | |
|---|---|
| *A01J 7/04* | (2006.01) |
| *A01J 5/04* | (2006.01) |
| *A61K 9/00* | (2006.01) |
| *A01J 5/007* | (2006.01) |
| *A01J 7/02* | (2006.01) |
| *F16L 55/07* | (2006.01) |

(52) U.S. Cl.
CPC .................. *A01J 7/04* (2013.01); *A01J 5/007* (2013.01); *A01J 5/044* (2013.01); *A01J 7/022* (2013.01); *A61K 9/0041* (2013.01); *F16L 55/07* (2013.01); *F16L 2201/20* (2013.01); *F16L 2201/30* (2013.01)

(58) Field of Classification Search
CPC ........ A01J 7/04; A01J 7/00; A01J 7/02; A01J 7/022; A01J 7/025; A01J 7/027; A01J 5/007; A01J 5/044
See application file for complete search history.

(56) References Cited

U.S. PATENT DOCUMENTS

| | | | |
|---|---|---|---|
| 1,365,665 A | 1/1921 | Davies |
| 2,012,031 A | 8/1935 | Woodruff |
| 2,532,088 A | 11/1950 | Cordis |
| 2,747,544 A | 5/1956 | Thomas |

(Continued)

FOREIGN PATENT DOCUMENTS

| | | |
|---|---|---|
| AU | 641229 | 9/1993 |
| AU | 2013294747 B2 | 11/2016 |

(Continued)

OTHER PUBLICATIONS

"Grade A pasteurized milk ordinance" 2003 Revision; US Department Health and Human Services, Public Health Service; Food and Drug Administration.

(Continued)

*Primary Examiner* — Kristen C Hayes
(74) *Attorney, Agent, or Firm* — Smith Law Office; Jeffry W. Smith

(57) ABSTRACT

A safety valve arrangement and method, having an upstream block valve, a downstream block valve, and a pressure monitored galley between the upstream valve and the downstream valve.

20 Claims, 30 Drawing Sheets

(56) References Cited

U.S. PATENT DOCUMENTS

| | | |
|---|---|---|
| 3,014,455 A | 12/1961 | Olander |
| 3,099,246 A | 7/1963 | Beskow |
| 3,119,401 A | 1/1964 | Merrit et al. |
| 3,285,297 A | 11/1966 | Duft et al. |
| 3,417,763 A | 12/1968 | Fjermestad et al. |
| 3,461,845 A | 8/1969 | Peterson |
| 3,474,760 A | 10/1969 | Siddall et al. |
| 3,482,547 A | 12/1969 | Maier |
| 3,500,839 A | 3/1970 | Bender |
| 3,630,081 A | 12/1971 | Nelson |
| 3,648,696 A | 3/1972 | Keith |
| 3,688,783 A | 9/1972 | Owens |
| 3,696,790 A | 10/1972 | Albright |
| 3,713,423 A | 1/1973 | Sparr, Sr. |
| 3,726,253 A | 4/1973 | Duncan |
| 3,762,371 A | 10/1973 | Quayle et al. |
| 3,789,798 A | 2/1974 | Reisgies et al. |
| 3,797,525 A | 3/1974 | Lieser |
| 3,861,335 A | 1/1975 | Przewalski |
| 3,861,355 A | 1/1975 | Johnson et al. |
| 3,957,018 A | 5/1976 | Barrett |
| 3,971,512 A | 7/1976 | Duncan |
| 3,973,520 A | 8/1976 | Flocchini |
| 3,989,009 A | 11/1976 | Robar et al. |
| 4,034,714 A | 7/1977 | Umbaugh et al. |
| 4,061,504 A | 12/1977 | Zall et al. |
| 4,149,489 A | 4/1979 | Umbaugh et al. |
| 4,168,677 A | 9/1979 | Brown |
| 4,175,514 A | 11/1979 | Souza et al. |
| 4,177,760 A | 12/1979 | Slater |
| 4,222,346 A | 9/1980 | Reisgies |
| 4,253,421 A | 3/1981 | Slater et al. |
| 4,254,754 A | 3/1981 | Takada et al. |
| 4,295,490 A | 10/1981 | Boudreau |
| 4,305,346 A | 12/1981 | Sparr, Sr. |
| 4,332,215 A | 6/1982 | Larson |
| 4,333,387 A | 6/1982 | Seitz |
| 4,333,421 A | 6/1982 | Schluckbier |
| 4,344,385 A | 8/1982 | Swanson et al. |
| 4,372,345 A | 2/1983 | Mehus |
| 4,378,757 A | 4/1983 | Hamann |
| 4,393,811 A | 7/1983 | Bodmin |
| 4,395,971 A | 8/1983 | Happel et al. |
| 4,403,568 A | 9/1983 | Fukuhara et al. |
| 4,403,569 A | 9/1983 | Bennett |
| 4,459,938 A | 7/1984 | Noorlander |
| 4,462,425 A | 7/1984 | Mehus |
| 4,485,762 A | 12/1984 | Sutton et al. |
| 4,498,419 A | 2/1985 | Flocchini |
| 4,516,530 A | 5/1985 | Reisgies et al. |
| 4,572,105 A | 2/1986 | Chowdhury et al. |
| 4,586,462 A | 5/1986 | Icking |
| 4,593,649 A | 6/1986 | Britten |
| 4,903,639 A | 2/1990 | Kessel |
| 4,907,535 A | 3/1990 | Matsuzawa et al. |
| 4,924,809 A | 5/1990 | Verbrugge |
| 4,936,254 A | 6/1990 | Marshall |
| 5,052,341 A | 10/1991 | Woolford et al. |
| 5,101,770 A | 4/1992 | Stevenson |
| 5,134,967 A | 8/1992 | Marshall |
| 5,161,482 A | 11/1992 | Griffin |
| 5,166,313 A | 11/1992 | Archibald et al. |
| 5,167,201 A | 12/1992 | Peles |
| 5,178,095 A | 1/1993 | Mein |
| 5,218,924 A | 6/1993 | Thompson et al. |
| 5,255,628 A | 10/1993 | Kristoffer |
| 5,379,722 A | 1/1995 | Larson |
| 5,386,799 A | 2/1995 | Dietrich |
| 5,390,627 A | 2/1995 | Van Der Berg et al. |
| 5,403,005 A | 4/1995 | Avila-Valdez |
| 5,493,995 A | 2/1996 | Chowdhury |
| 5,568,788 A | 10/1996 | Van Den Berg et al. |
| 5,572,947 A | 11/1996 | Larson et al. |
| 5,673,650 A | 10/1997 | Mottram et al. |
| 5,697,325 A | 12/1997 | Gehm et al. |
| 5,722,343 A | 3/1998 | Aurik et al. |
| 5,769,025 A | 6/1998 | Van Der Lely et al. |
| 5,778,820 A | 7/1998 | Van Der Lely et al. |
| 5,850,845 A | 12/1998 | Pareira et al. |
| 5,881,669 A | 3/1999 | Van Den Berg et al. |
| 5,896,828 A | 4/1999 | Kronschnabel et al. |
| 5,909,716 A | 6/1999 | Van Der Lely |
| 5,934,220 A | 8/1999 | Hall et al. |
| 5,957,081 A | 9/1999 | Van Der Lely et al. |
| 5,960,736 A | 10/1999 | Ludington et al. |
| 5,992,347 A | 11/1999 | Innings et al. |
| 6,009,833 A | 1/2000 | Van Der Lely |
| 6,079,359 A | 6/2000 | Van Den Berg |
| 6,089,242 A | 7/2000 | Buck |
| 6,098,570 A | 8/2000 | Aurik et al. |
| 6,202,593 B1 | 3/2001 | Maier et al. |
| 6,234,110 B1 | 5/2001 | Xavier |
| 6,244,215 B1 | 6/2001 | Oosterling |
| 6,267,077 B1 | 7/2001 | Van Den Berg et al. |
| 6,276,297 B1 | 8/2001 | Van Den Berg et al. |
| 6,308,655 B1 | 10/2001 | Oosterling |
| 6,318,299 B1 | 11/2001 | Birk |
| 6,321,682 B1 | 11/2001 | Eriksson et al. |
| 6,367,416 B1 | 4/2002 | Van Der Lely |
| 6,371,046 B1 | 4/2002 | Petterson et al. |
| 6,435,132 B1 | 8/2002 | Milbrath et al. |
| 6,546,893 B1 | 4/2003 | Happel et al. |
| 6,550,420 B1 | 4/2003 | Bjork |
| 6,561,126 B2 | 5/2003 | Forsen et al. |
| 6,584,930 B2 | 7/2003 | Buecker |
| 6,591,784 B1 | 7/2003 | Eriksson |
| 6,598,560 B1 | 7/2003 | Van Den Berg |
| 6,619,227 B1 | 9/2003 | Berger et al. |
| 6,626,130 B1 | 9/2003 | Eriksson |
| 6,644,240 B1 | 11/2003 | Dietrich |
| 6,752,102 B2 | 6/2004 | Dahl et al. |
| 6,755,153 B1 | 6/2004 | Chowdhury |
| 6,935,270 B2 | 8/2005 | Wipperfurth et al. |
| 6,997,135 B1 | 2/2006 | DeWaard |
| 6,997,136 B1 | 2/2006 | Coates |
| 7,036,981 B2 | 5/2006 | Veenstra et al. |
| 7,128,020 B2 | 10/2006 | Björk et al. |
| 7,143,718 B2 | 12/2006 | Bosma et al. |
| 7,162,970 B2 | 1/2007 | Maier, Jr. |
| 7,174,848 B2 | 2/2007 | Brown et al. |
| 7,178,480 B2 | 2/2007 | Dahl et al. |
| 7,237,694 B2 | 7/2007 | Freudinger |
| 7,263,948 B2 | 9/2007 | Ericsson et al. |
| 7,281,493 B2 | 10/2007 | Dietrich |
| 7,290,497 B2 | 11/2007 | Rottier et al. |
| 7,299,766 B2 * | 11/2007 | Van Den Berg ...... A01J 5/0175 119/14.02 |
| 7,350,478 B2 | 4/2008 | Fernandez |
| 7,377,232 B2 | 5/2008 | Holmgren et al. |
| 7,401,573 B2 | 7/2008 | Torgerson |
| 7,412,943 B2 | 8/2008 | Ericsson et al. |
| 7,484,474 B2 | 2/2009 | Van Den Berg et al. |
| 7,536,975 B2 | 5/2009 | Denes et al. |
| 7,575,022 B2 | 8/2009 | Higgins |
| 7,578,260 B2 | 8/2009 | Shin |
| 7,707,966 B2 | 5/2010 | Torgerson et al. |
| 7,765,951 B2 | 8/2010 | Dietrich |
| 7,793,614 B2 | 9/2010 | Ericsson et al. |
| 7,926,449 B2 | 4/2011 | Stellnert et al. |
| 7,963,249 B2 | 6/2011 | Duke |
| 8,025,029 B2 | 9/2011 | Torgerson et al. |
| 8,033,247 B2 | 10/2011 | Torgerson et al. |
| 8,117,989 B2 | 2/2012 | Torgerson et al. |
| 8,210,123 B2 | 7/2012 | Duke |
| 8,240,272 B2 | 8/2012 | Duke |
| 8,342,125 B2 | 1/2013 | Torgerson et al. |
| 8,590,486 B2 | 11/2013 | Torgerson et al. |
| 8,677,937 B2 | 3/2014 | Shin |
| 8,770,146 B2 | 7/2014 | Buck et al. |
| 8,925,483 B2 | 1/2015 | Torgerson et al. |
| 8,991,335 B2 | 3/2015 | Torgerson et al. |
| 9,016,238 B2 | 4/2015 | Duke |
| 9,049,835 B2 | 6/2015 | Duke |
| 9,072,272 B2 * | 7/2015 | Bosma .................... A01J 7/022 |

(56) References Cited

U.S. PATENT DOCUMENTS

| | | | |
|---|---|---|---|
| 9,072,273 | B2 | 7/2015 | Torgerson et al. |
| 9,332,726 | B2 * | 5/2016 | Bosma ................ A01J 5/0134 |
| 9,468,189 | B2 | 10/2016 | Toregrson et al. |
| 9,468,190 | B2 | 10/2016 | Duke |
| 9,510,556 | B2 | 12/2016 | Torgerson et al. |
| 9,526,224 | B2 | 12/2016 | Balkenhol et al. |
| 9,545,079 | B2 | 1/2017 | Torgerson et al. |
| 9,686,958 | B2 * | 6/2017 | Sellner ................ A01J 5/01 |
| 9,763,421 | B2 | 9/2017 | Torgerson et al. |
| 9,770,006 | B2 | 9/2017 | Torgerson et al. |
| 9,883,652 | B2 | 2/2018 | Torgerson et al. |
| 9,930,862 | B2 | 4/2018 | Torgerson et al. |
| 10,123,506 | B2 | 11/2018 | Bosma |
| 10,426,128 | B2 | 10/2019 | Balkenhol et al. |
| 10,499,610 | B2 | 12/2019 | Toregrson et al. |
| 10,502,330 | B2 | 12/2019 | Balkenhol |
| 10,514,316 | B2 * | 12/2019 | Enickl ................ A01J 7/00 |
| 10,681,895 | B2 | 6/2020 | Sellner et al. |
| 2002/0185071 | A1 | 12/2002 | Guo |
| 2004/0089242 | A1 | 5/2004 | Verstege et al. |
| 2004/0231603 | A1 | 11/2004 | Bjork et al. |
| 2005/0274327 | A1 | 12/2005 | Johnsson et al. |
| 2006/0016399 | A1 | 1/2006 | Torgerson |
| 2006/0037542 | A1 | 2/2006 | Denes et al. |
| 2006/0112887 | A1 | 6/2006 | Brown et al. |
| 2007/0070803 | A1 | 3/2007 | Urquhart |
| 2007/0157887 | A1 | 7/2007 | Fernandez |
| 2007/0186860 | A1 | 8/2007 | Dietrich |
| 2007/0215053 | A1 | 9/2007 | Duke |
| 2007/0277737 | A1 | 12/2007 | Maier et al. |
| 2008/0022932 | A1 | 1/2008 | Rottier et al. |
| 2008/0202433 | A1 | 8/2008 | Duke |
| 2008/0276871 | A1 | 11/2008 | Auburger et al. |
| 2008/0314322 | A1 | 12/2008 | Stellnert et al. |
| 2009/0050061 | A1 | 2/2009 | Duke |
| 2009/0050062 | A1 | 2/2009 | Auburger et al. |
| 2009/0064937 | A1 | 3/2009 | Rottier et al. |
| 2009/0151641 | A1 | 6/2009 | Schulze Wartenhorst et al. |
| 2009/0165724 | A1 | 7/2009 | Mader et al. |
| 2009/0320760 | A1 | 12/2009 | Torgerson et al. |
| 2010/0132626 | A1 | 6/2010 | Torgerson et al. |
| 2010/0154900 | A1 | 6/2010 | Torgerson et al. |
| 2010/0236487 | A1 | 9/2010 | Stellnert et al. |
| 2010/0326360 | A1 | 12/2010 | Duke et al. |
| 2011/0220028 | A1 | 9/2011 | Duke |
| 2011/0220160 | A1 * | 9/2011 | Bosma ................ A01J 7/022 |
| | | | 134/56 R |
| 2011/0232575 | A1 | 9/2011 | Duke |
| 2012/0111275 | A1 | 5/2012 | Torgerson et al. |
| 2012/0118237 | A1 | 5/2012 | Torgerson et al. |
| 2012/0118238 | A1 | 5/2012 | Torgerson et al. |
| 2012/0272911 | A1 | 11/2012 | Duke |
| 2013/0199449 | A1 | 8/2013 | Daniel |
| 2014/0283751 | A1 | 9/2014 | Buck et al. |
| 2015/0173320 | A1 | 6/2015 | Balkenhol et al. |
| 2015/0201577 | A1 | 7/2015 | Duke |
| 2015/0260302 | A1 | 9/2015 | Peterson et al. |
| 2016/0319947 | A1 | 11/2016 | Balkenhol |
| 2017/0014837 | A1 | 1/2017 | Duke |
| 2017/0164576 | A1 | 6/2017 | Balkenhol et al. |
| 2017/0359995 | A1 | 12/2017 | Sellner et al. |
| 2018/0064056 | A1 | 3/2018 | Torgerson et al. |
| 2018/0220616 | A1 | 8/2018 | Torgerson et al. |
| 2018/0235173 | A1 | 8/2018 | Torgerson et al. |
| 2019/0133067 | A1 | 5/2019 | Stuessel et al. |
| 2019/0133069 | A1 | 5/2019 | Stuessel et al. |
| 2019/0145531 | A1 | 5/2019 | Balkenhol et al. |
| 2020/0088310 | A1 | 3/2020 | Balkenhol |
| 2020/0352129 | A1 | 11/2020 | Torgerson et al. |

FOREIGN PATENT DOCUMENTS

| | | |
|---|---|---|
| AU | 2015227478 B2 | 6/2018 |
| DE | 1801758 | 6/1970 |
| DE | 1582939 | 7/1970 |
| DE | 2622794 | 12/1977 |
| DE | 3540058 | 5/1987 |
| DE | 261300 | 10/1988 |
| DE | 4006785 | 9/1990 |
| DE | 10160161 A1 | 6/2003 |
| DE | 102013114595 A1 | 6/2015 |
| EP | 0277396 A1 | 8/1988 |
| EP | 0313109 A1 | 4/1989 |
| EP | 0319523 A2 | 6/1989 |
| EP | 0332235 A2 | 9/1989 |
| EP | 0459817 A2 | 12/1991 |
| EP | 0479397 A2 | 4/1992 |
| EP | 0527509 A2 | 2/1993 |
| EP | 0543463 A1 | 5/1993 |
| EP | 0583166 A2 | 2/1994 |
| EP | 0630557 A2 | 12/1994 |
| EP | 0728412 A2 | 8/1996 |
| EP | 0801893 A2 | 10/1997 |
| EP | 0945057 A1 | 9/1999 |
| EP | 1001199 A2 | 5/2000 |
| EP | 1219167 A2 | 7/2002 |
| EP | 1222853 A2 | 7/2002 |
| EP | 1089615 B1 | 3/2003 |
| EP | 1520469 A1 | 4/2005 |
| EP | 1543720 A1 | 6/2005 |
| EP | 1790217 A2 | 5/2007 |
| EP | 1795069 A1 | 6/2007 |
| EP | 1679956 B1 | 12/2008 |
| EP | 2113169 A1 | 11/2009 |
| EP | 1933616 B1 | 1/2011 |
| EP | 2277373 A2 | 1/2011 |
| EP | 1737291 B1 | 11/2013 |
| GB | 918766 | 2/1963 |
| GB | 1160900 | 8/1969 |
| GB | 1440901 | 6/1976 |
| GB | 0324647.7 | 10/2003 |
| GB | 0402119.2 | 1/2004 |
| GB | 0408968.6 | 4/2004 |
| GB | 0417392.8 | 4/2004 |
| JP | 2002345955 | 12/2002 |
| JP | 2002354958 | 12/2002 |
| JP | 2005192404 | 7/2005 |
| NL | 1016237 | 3/2002 |
| NL | 1021950 C | 5/2004 |
| SU | 1676538 | 9/1991 |
| WO | 1993/13651 | 7/1993 |
| WO | 1998/28969 | 7/1998 |
| WO | 1999/27775 | 6/1999 |
| WO | 1999/46978 | 9/1999 |
| WO | 1999/66767 | 12/1999 |
| WO | 1999/66787 | 12/1999 |
| WO | 01/17337 | 3/2001 |
| WO | 01/17338 | 3/2001 |
| WO | 02/07506 | 1/2002 |
| WO | 02/23976 | 3/2002 |
| WO | 03/030630 | 4/2003 |
| WO | 03/077645 | 9/2003 |
| WO | 03/098998 | 12/2003 |
| WO | 04/032608 | 4/2004 |
| WO | 2004/030445 A2 | 4/2004 |
| WO | 05/022986 | 3/2005 |
| WO | 05/043986 | 5/2005 |
| WO | 05/072516 | 8/2005 |
| WO | 05/102035 | 11/2005 |
| WO | 2006/029797 | 3/2006 |
| WO | 2006/091710 A2 | 8/2006 |
| WO | 2006/110079 A1 | 10/2006 |
| WO | 2006/117019 | 11/2006 |
| WO | 2006/135917 | 12/2006 |
| WO | 2007/031783 | 3/2007 |
| WO | 2007/129884 | 11/2007 |
| WO | 2007/129888 | 11/2007 |
| WO | 2008/102567 | 8/2008 |
| WO | 2008/138862 | 11/2008 |
| WO | 2009/077607 | 6/2009 |
| WO | 2009/158000 | 12/2009 |
| WO | 2010/053577 | 5/2010 |
| WO | 2011/28292 | 3/2011 |

(56) References Cited

FOREIGN PATENT DOCUMENTS

| WO | 2011/28293 | 3/2011 |
|---|---|---|
| WO | 2011/28294 | 3/2011 |
| WO | 2011102911 | 8/2011 |
| WO | 2014/016588 A1 | 1/2014 |
| WO | 2015/118336 A1 | 2/2015 |
| WO | 2015/145116 A1 | 10/2015 |
| WO | 2015/150807 A1 | 10/2015 |
| WO | 2017/191057 A1 | 11/2017 |
| WO | 2019/090044 A1 | 5/2019 |
| WO | 2019/090136 A9 | 5/2019 |

OTHER PUBLICATIONS

"3-A® Accepted Practices for Permanently Installed Product and Solution Pipelines and Cleaning Systems Used in Milk and Milk Product Processing Plants, No. 605-04," Section N; Aug. 20, 1994.
Akam, D.N., "The Development of Equipment for the Mechanization of Manual Operations in Milking Machine," 17th Annual Meeting, National Mastitis Counsel, Inc., Feb. 21-23, 1978, pp. 417-426.
Grindal; et al., "Automatic application of teat disinfectant through the milking machine cluster" Journal of Dairy Research, 56:579-585 (1989).
International Search Report and Written Opinion from PCT/US2011/00322, dated Dec. 20, 2011.
Letter to Alex Ferguson from Jeffry W. Smith dated Dec. 22, 2006, 2pp.
Neijenhuis; et al., "Health of dairy cows milked by an automatic milking system; Effects of milking interval on teat condition and milking performance with whole-udder take off", Oct. 2003, 23 pages.
Office Action for U.S. Appl. No. 10/576,744 dated Jun. 3, 2010, 8pp.
Office Action for U.S. Appl. No. 11/652,372 dated Feb. 11, 2008, 14pp.
Office Action for U.S. Appl. No. 11/662,454 dated Aug. 16, 2010, 20 pp.
Office Action for U.S. Appl. No. 11/904,769 dated Feb. 20, 2008, 9pp.
Office Action for U.S. Appl. No. 12/712,787 dated Jun. 27, 2011.
PCT/GB04/004343—Written Opinion of ISA & IPRP, dated Feb. 3, 2005, 5pp.
"PCT/US06/023075—ISR & Written Opinion dated Oct. 16, 2006".
PCT/US09/006026—IPRP, Written Opinion of ISA & ISR dated Mar. 6, 2010, 9pp.
"PCT/US09/03770—IPRP and Written Opinion dated Jan. 13, 2011, and ISR".
Preliminary Amendment for U.S. Appl. No. 10/576,744, filed Apr. 21, 2006, 16pp.
Preliminary Amendment for U.S. Appl. No. 10/576,744, filed Aug. 7, 2008, 10 pp.
Shearn; et al., "Reduction of bacterial contamination of teat cup liners by an entrained wash system," Veterinary Record (1994), 134, 450, 1p.
Thompson; et al. "The End-Of-Milking Sequence and its Mechanization" 1976 Winter Mtg., Dec. 14-17, 1976, Animal Physiology and Genetics Inst., Beltsville, MD, 15pp.
U.S. Appl. No. 60/566,313, filed Apr. 29, 2004, J.R.J. Duke.
U.S. Appl. No. 60/566,314, filed Apr. 29, 2004, J.R.J. Duke.
U.S. Appl. No. 60/578,997, filed Jun. 12, 2004, Kevin L. Torgerson.
Notice of Opposition and Opposition brief for EP Patent 1737291, Filed on Aug. 26, 2014 by GEA Farm Technologies GmbH, 74 pages.
Response filed Feb. 2, 2015 by an Udder IP Company in the Opposition of EP Patent 1737291, 53 pages.
European Search Report dated Sep. 24, 2015 for EP Application No. 15171008.4, 6 pages.
Reply filed on Dec. 16, 2015 by GEA Farm Technologies GmbH in the Opposition of EP Patent No. 1737291, 75 pages.
Wildbrett et al., "Über Reinigung and Desinfektion von Tanks" Materials and Corrosion 12(12):759-764. Nov. 1961.
European Patent Office Preliminary Opinion and Summons to Attend Oral Proceedings dated Jan. 18, 2016, Opposition of EP Patent 1737291, 12 pages.
European Search Report dated Aug. 13, 2014, EP Application No. 14159588.4, 5 pages.
International Search Report and Written Opinion from PCT/EP2014/077684, dated Apr. 10, 2015, 10 pages.
International Search Report and Written Opinion from PCT/US2018/058897, dated Feb. 25, 2019, 19 pages.
International Search Report and Written Opinion from PCT/US2018/059041, dated Mar. 8, 2019, 20 pages.
Amendments and Observations filed Oct. 24, 2016 by An Udder IP Company Ltd in the Opposition of EP Patent 1737291, 47 pages.
Amendments and Observations filed Oct. 25, 2016 by GEA Farm Technologies GmbH in the Opposition of EP Patent 1737291, 13 pages.
Nov. 10, 2016 EPO Communication re: the Proprietor, An Udder IP Company Ltd's request concerning the staying/postponement of the opposition proceedings, Opposition of EP Patent 1737291, 1 page.
Nov. 25, 2016 EPO Communication re: results of the oral proceedings, Opposition of EP Patent 1737291, 5 pages.
Dec. 8, 2016 EPO Communication; Details and minutes of the oral proceedings, Opposition of EP Patent 1737291, 13 pages.
Mar. 30, 2017 EPO Communication, State of the Opposition Procedure and Invitation to File Observations, Opposition of EP Patent 1737291, 10 pages.
Response filed by Udder IP Company Ltd dated Jun. 2, 2017, Opposition of EP Patent 1737291, 4 pages.
Response filed by GEA Farm Technologies GmbH dated May 29, 2017, Opposition of EP Patent 1737291, 5 pages.
Jul. 27, 2017 EPO Communication; State of the Opposition Procedure and Summons to Attend Oral Proceedings, Opposition of EP Patent 1737291, 10 pages.
European Search Report dated Oct. 13, 2017, for European Application No. 17171229.2, 6 pages.
Mar. 13, 2018 Letter from the Proprietor, An Udder IP Company Ltd, Regarding the Opposition Procedure for Opposition of EP Patent 1737291, 23 pages.
May 17, 2018 EPO Communication; Details and minutes of the oral proceedings, Opposition of EP Patent 1737291, 9 pages.
May 31, 2018 Interlocutory Decision in Opposition Proceedings, Opposition of EP Patent 1737291, 49 pages.
Sep. 27, 2018 Statement of Grounds for Appeal, Opposition of EP Patent 1737291, 29 pages.
Feb. 4, 2019 Reply to Grounds for Appeal, Opposition of EP Patent 1737291, 32 pages.
International Search Report for PCT/EP2017/060232, dated Aug. 3, 2017, 2 pages.
German Search Report for DE Application No. 10 2016 108 300.3, dated Mar. 10, 2017, 7 pages.
European Search Report dated Jan. 30, 2020 for European Application No. 19204875.9, 6 pages.
International Preliminary Report on Patentability for International Application No. PCT/US2018/059041, dated May 5, 2020, 12 pages.
International Preliminary Report on Patentability for International Application No. PCT/US2018/058897, dated May 5, 2020, 10 pages.
Mar. 20, 2020 Examination Report for Australian Application No. 2018211343, 7 pages.
Oct. 15, 2020 Communiation Regarding Oral Proceedings in Opposition to EP Patent 1737291, 10 pages.
Office Action for U.S. Appl. No. 16/178,996 dated Jun. 24, 2021.

* cited by examiner

AUTOMATED MILKING SYSTEM SAFETY VALVE ARRANGEMENT

CROSS REFERENCE TO RELATED APPLICATION

This application claims the benefit of U.S. Provisional Application 62/581,514, filed Nov. 3, 2017, and U.S. Provisional Application 62/581,526, filed Nov. 3, 2017, the disclosures of which are incorporated by reference herein.

FIELD AND BACKGROUND OF THE INVENTION

The present invention relates generally to safety valves for segregating dairy milk lines from contamination by other fluids such as teat dips, and more particularly to safety valves with improved safety and monitoring features.

Dairy milking systems as they relate to the present invention include a cluster of teat cups, each of which is matched with a flexible teat cup liner that is attached to a teat of a dairy animal with a vacuum. Vacuum is applied in pulses between the shell and liner to facilitate movement of the flexible liner to milk the dairy animals. Milk flows from the dairy animal through each flexible liner and then through a milk tube to a milker unit collecting assembly, which collects milk from all of the animal's teats. This combination of elements is known as a milker unit and can be used to milk cows, sheep, goats and other dairy animals. Each milker unit is used to milk multiple animals so it must be sanitized, at least periodically, to prevent transmission of dirt and germs into the milk, and to help prevent transmission of diseases from animal to animal.

Milk from individual animals flows from each collecting assembly through milk tubes and into a milk line that receives milk from all of the milker units in the dairy. The milk is then chilled and stored in a milk tank. The milk lines and storage systems must not be contaminated with dirt, debris, chemicals, pathogens, or contaminated milk. In the event that milk being collected is from a sick dairy animal, or a monitoring system determines the milk is unsellable, the milk would be diverted to a "bad milk" line or a milk line for feeding to calves—a "calf milk" line.

Traditionally, dairy animal teats have been prepared for milking by cleaning the teats before milking using sanitizing teat dips, and protecting teats after milking by applying protective teat dips. These dips are broadly categorized as "pre-dips" and "post-dips." Before automated systems were used, the pre-dips and post-dips were applied by dairy operators manually, with cloth wipes or specialized teat dip applicators. The teat dips were effective in cleaning and protecting teats from infection, but as automated milking systems came into commercial use, automated teat dip applicators were developed to realize the full benefit of automated milking.

Various types of automated (robotic) milking systems have been developed with automated systems for applying teat dip, air, and rinsing fluids (referred to herein as "teat dip fluids") applied and rinsed from the system in a manner that protects milk lines, and the milk therein, from being contaminated. Protecting milk lines and milk is mandated in the United States Food and Drug Administration's Pasteurized Milk Ordinance ("PMO"), Item 14r., for example, as well as other regulatory agencies throughout the world.

To protect milk lines in the United States, they should be separated from potentially contaminating fluids using at least two automatically controlled valves or a double seat mixproof valve, with a drainable opening to the atmosphere between the valves or seats (PMO Item 14r.) This arrangement is referred to as "block-bleed-block," and protects milk lines from contamination even when the valves or valve seats fail by draining fluid through the opening (bleed) rather than allowing it to pass through both valves or valve seats. Various embodiments of block-bleed-block valves and valve arrangements are known and operate effectively. See for example: U.S. Pat. Nos. 8,342,125; 9,510,556; and 9,686,958.

Milk line protection systems can be complicated because pre-dipping and post-dipping require that teat dipping fluids be delivered in precise dosages and in a timely fashion to provide proper teat treatment, system cleaning, system timing, and milk line protection. Dosage valves for teat dips measure proper dosage quantities of teat dips and ensure that the doses are delivered under pressure and timing. Air can be used to "chase" the teat dip. Following teat dip application, the delivery system must be sufficiently cleaned and rinsed with water or other rinsing fluid, to sanitize equipment before subsequent milkings.

Further complicating teat dip delivery systems is the requirement that the teat dip, air, and water provided from main source lines must be accurately divided and delivered to each teat of the dairy animal. Typically, dividing dosages of teat dip fluids is performed through a teat dip fluid manifold that receives the fluids from one or more main supply lines and then divides the fluids into individual delivery lines. Given the short time durations in which teat dip must pass through the teat dip fluid manifold, providing adequate milk line protections can be challenging.

Further complicating teat dip fluid delivery systems, is a desire to prevent cross-contamination of the various teat dip fluids. For example, water should not be allowed to contaminate teat dip before it is delivered to a teat because the dip can be diluted and possibly less effective. Conversely, teat dip should not be allowed to contaminate water and air lines, which could foul the system and require additional maintenance. Also, pre-dips should not be contaminated by post-dips, which could contain iodine or other antimicrobial composition.

Safety valves are known in a number of different configurations, including those disclosed in U.S. Pat. Nos. 8,342,125 and 9,686,958. These safety valves are reliable and work flawlessly. Nonetheless, teat dips and/or backflushing fluids can have an adverse effect on valve seals. In particular, valve seals exposed to some teat dips could deteriorate and require regular maintenance. Other valve seal materials can swell when exposed to teat dips. When seals of this type are used in shuttle valves or are otherwise expected to slide on a sealing surface, the seal can inhibit valve operation and even cause spool-type valves (or 2 position-5 way valves) to seize.

Valve seal orientations, such as in a stationary valve head seat, are not susceptible to valve seizures due to swelling because the valve head will still seal securely even on a swollen seal. Unfortunately, such valve configurations are more difficult and space-consuming to configure in a safety valve.

In addition, block-bleed-block valve configuration required by The Pasteurized Milk Ordinance ("PMO") 14r.2.b.3. work effectively to "bleed" fluids that seep past one of the "block" valves, but the vent used to bleed leaked fluids are difficult to monitor. Consequently, leaking block valves in a safety valve can escape notice when maintenance is required.

Therefore, there is a need for an improved dairy system safety valve that requires reduced maintenance, is relatively compact, and can be readily monitored for possible leakage.

SUMMARY OF THE INVENTION

A valve assembly in accordance with the present invention includes: a conduit defining a flow path having a first end and a second end; a first valve having an open position and a closed position to close the first end of the flow path; a second valve having an open position and a closed position to close the second end of the flow path; a pressurized fluid source in fluid communication with the flow path when the first valve is closed and the second valve is closed; and a pressure monitor in communication with the flow path to determine fluid pressure in the flow path. This safety valve is an improvement over the prior block-bleed-block valve arrangements because the vent to atmosphere is replaced with an active pressurized zone in between two closed valves to define a beneficial arrangement of a block-monitor-block, the benefits of which include active valve monitoring, detection of valve leaks for improved and timely maintenance, and improved safety that forces pressurized gas upstream through a leaky upstream valve or downstream through a leaky downstream valve.

The valve assembly pressure monitor can generate data corresponding to fluid pressure in the flow path, and the data is compared to a predetermined fluid pressure. The pressure sensor can generate data corresponding to fluid pressure in the flow path, and the valve assembly can further include: a controller that compares the data to a predetermined flow channel pressure range and generates a signal if the data comparison indicates that the data is outside of the predetermined range.

The valve assembly first valve can be a two-position, three-way valve, and the second valve can be a two-position, three-way valve.

In an alternate embodiment, the first valve is a shuttle valve, and the second valve is a shuttle valve.

Further, the pressurized fluid source can communicate pressurized gas to the flow path when the first valve is in the closed position and the second valve is in the closed position.

The present safety valve invention is described and depicted herein for use in a teat dip fluid dispensing system. Nonetheless, the safety valve is intended to be used in a variety of dairy settings including, but not limited to, teat dip dispensing; milk lines handling good, bad, or calf milk; and any other situation where good milk lines are to be protected from contamination.

Other features and benefits of the invention will be apparent from the following Detailed Description of the Drawings.

DETAILED DESCRIPTION OF THE INVENTION

Figure 1:
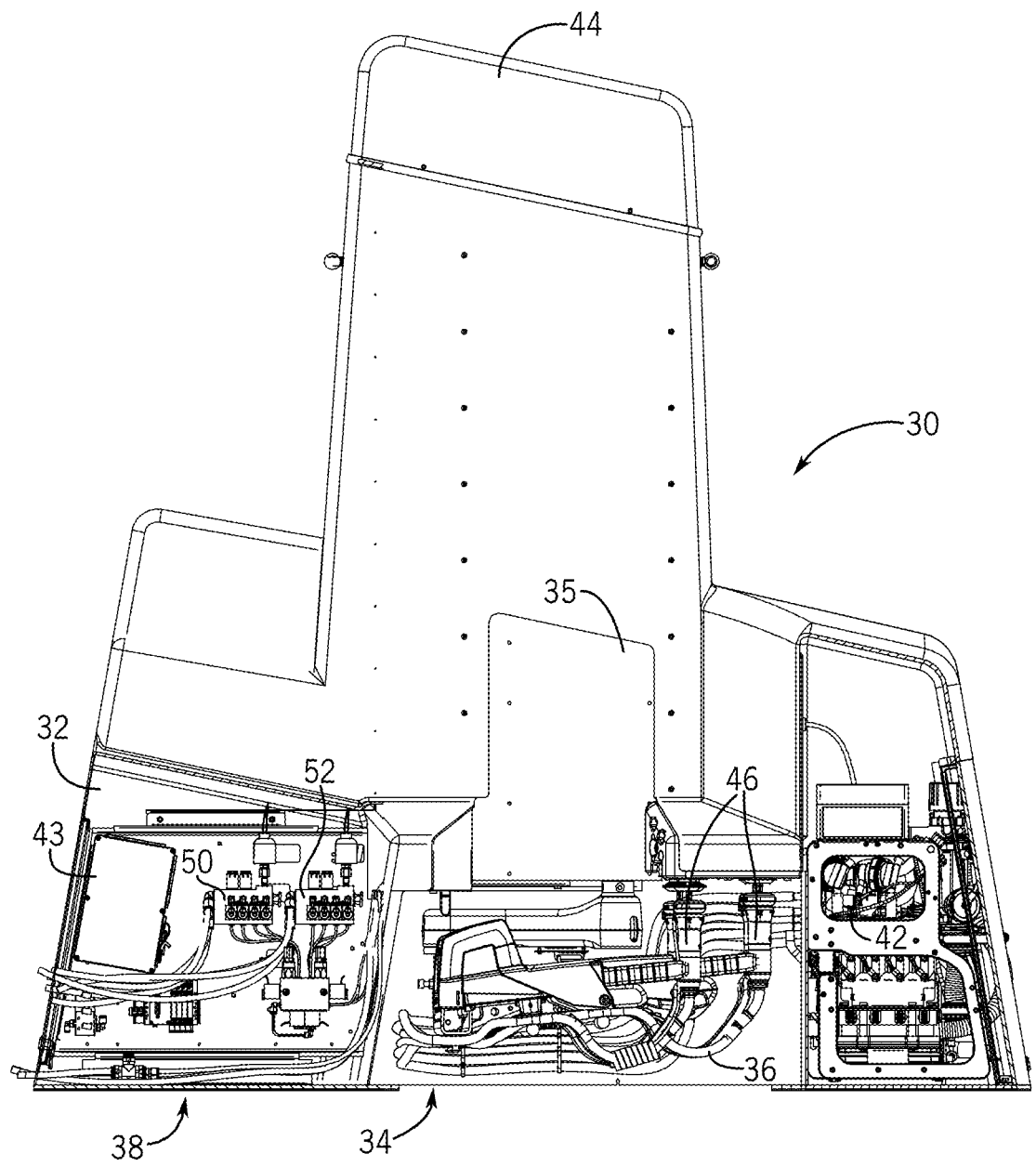
FIG. 1 is a perspective view of a dairy animal milking station having safety valves in accordance with the present invention.

In the following detailed description of the drawings, the same reference numeral may be used to designate the same or similar item in more than one figure. Also, the term "safety valve" may be used to designate an assemblage of valves or valve components, which may or may not be in a single valve housing. Individual safety valve components may also be referred to as "valves."

Illustrated generally in FIG. 1 is an automated dairy animal milking stall unit 30 used in a dairy harvesting facility. The dairy animal milking stall unit 30 can be used in any type of dairy arrangement, including those with stationary or rotary milking stalls, and the present invention is not limited for use in the particular type of milking stall unit 30 depicted herein.

The automated dairy animal milking stall unit 30 includes: a frame 32 for mounting in or adjacent to a milking stall; a milker unit 34 mounted in the frame 32; milk lines 36 as part of the milker unit 34; milker arm controls 35 used to control movement of the milker unit 34 between a parked position (shown) and a milking position (not shown); and a teat dip fluid supply system 38. Further, the frame 32 carries a milking module 42 for determining whether to direct milk to a "good milk" path, a "bad milk" path, or a "calf milk" path, for example. Also included, is a dipping module 43 that is programmed to monitor and control teat dipping, rinsing, and backflushing. The milking module 42 and the dipping module 43 are in communication with each other and coordinated by a programmable stall control 44, preferably concealed in an upper portion of the frame 32. It is preferred that all of the components described above be disposed in a single frame 32, but multiple frames or mounting systems can be used, so long as the teat dip fluid supply system 38 is in fluid communication with the milker unit 34 or at least a teat dip delivery unit for delivering pre-dip, post-dip, or both types of dip to a dairy animal's teats that will be milked using the milker unit 34.

The frame 32 can be open or enclosed or at least partially enclosed to protect the teat dip supply system 38, the milker unit control mechanism 42, and the programmable stall control 44 from the harsh dairy environment and from being damaged by dairy animals.

The milker unit 34 can be of any suitable design and preferably includes teat cups and liner combinations 46, each of which receives an animal teat for milking. Generally, milk travels from the liner through the milk lines 36 and downstream to suitable chilling and storage systems.

Preferably, the milker unit 34 also carries one or more hoses and teat dip delivery nozzles or openings to direct teat dip toward each animal teat. Also, preferably, the teat dip delivery nozzles or openings are formed in a teat cup liner, examples of such liners are disclosed in Torgerson et al., U.S. Pat. No. 8,991,335, but other types of dispensers and/or liners can be used with the present invention.

Figure 2:
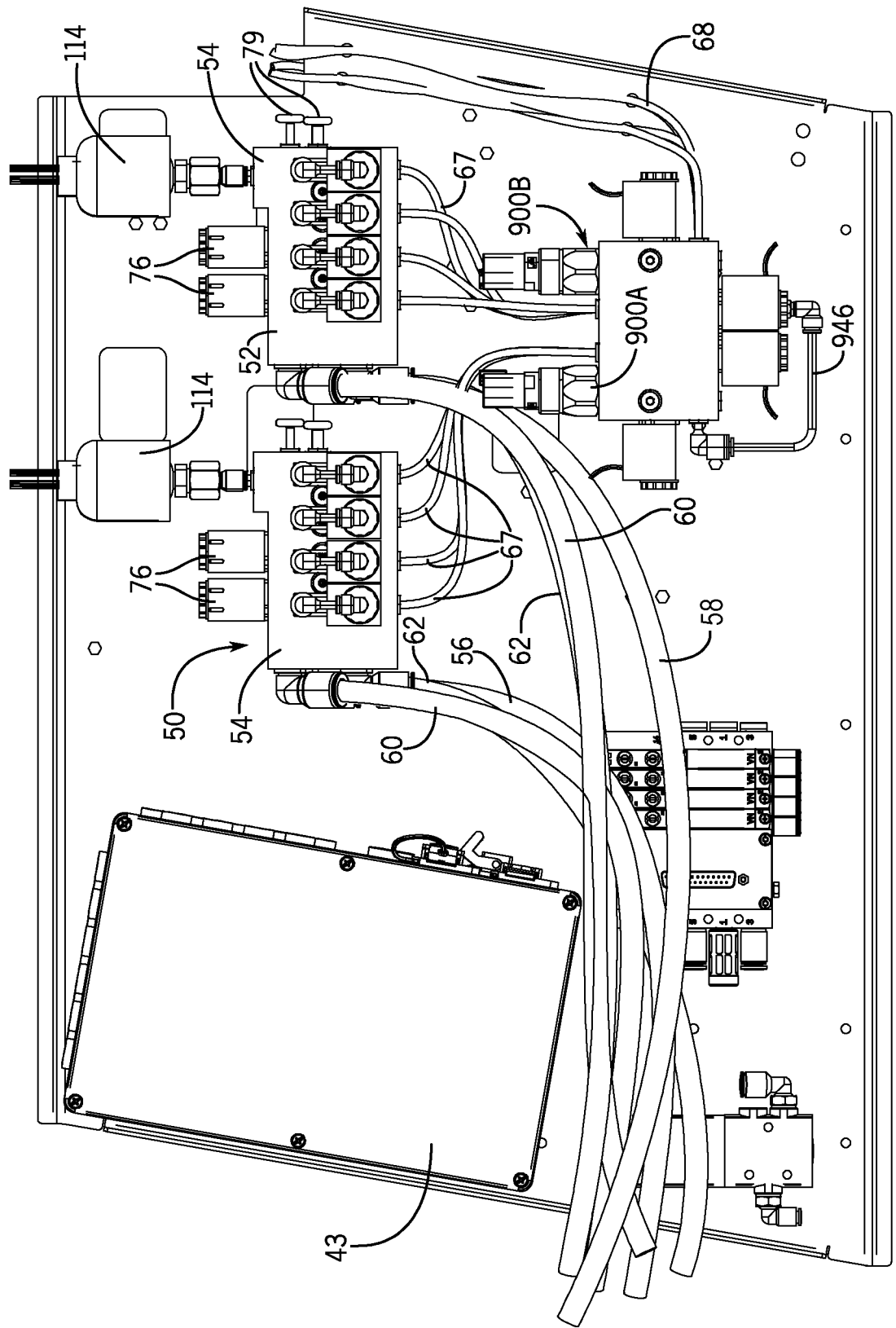
FIG. 2 is a front view of the safety valve from the milking station of FIG. 1.

To receive teat dip fluids such as teat dip, air, and rinsing fluids from appropriate sources and delivering them to individual dairy animal teats, the present invention includes at least one teat dip fluid manifold 50, and the embodiment depicted in FIGS. 1 and 2, includes a second teat dip fluid manifold 52. The first teat dip fluid manifold 50 delivers pre-dip fluids, and the second teat dip fluid manifold 52 delivers post-dip fluids. As described below, other embodiments of teat dip fluid manifolds can dispense both pre-dip fluids and post-dip fluids.

As used herein "teat dip fluids" can include teat dip for being applied before ("pre") or after ("post") milking, as well as, air to force teat dip through delivery lines, and rinsing fluids, such as water, for rinsing the teat dip fluid manifold, valves, delivery lines, and teat dip openings or nozzles. It is not necessary that all of these teat dip fluids be utilized in a single manifold 50, 52, but the present invention can be used to deliver one or more of these fluids effectively, efficiently, and reliably. Suitable manifolds are disclosed in a patent application entitled "Automated Teat Dip Fluid Manifold" filed on Nov. 3, 2017, and naming inventors Matthew J. Stuessel, Wolfgang Schulze-Wilmert, and Thomas Orban, which is incorporated herein by reference.

The first teat dip fluid manifold 50 and the second teat dip fluid manifold 52 can each have substantially the same construction or any other suitable construction in accordance with the present invention. The teat dip fluid manifold 50 includes a housing 54, a teat dip supply line 56 (a teat dip supply line 58 is shown for the second teat dip manifold 52), an air supply line 60, and a rinsing fluid supply line 62. Fewer or other fluids can also be supplied to the teat dip fluid manifold 50, if desired. Further, if only a single teat dip manifold 50 is used, the teat dip supply line 56 could be divided into two teat dip supply lines with corresponding inlets, so that one receives pre-dip and the other receives post-dip.

Generally, the manifolds 50 and 52 inlets for air and rinsing fluids are controlled by valves 76. Teat dip, air, and rinsing fluids are dispensed using an upstream valve (inside the housing 54) and a downstream valve 99, as seen in FIG. 2. A galley (not illustrated) between the various valves is monitored for pressure anomalies by a pressure monitor 114 to provide data to a controller 43, for example.

Once the fluids are dispensed through the manifolds 50/52, they are delivered to individual delivery lines 68 and then to appropriate nozzles in the teat cup liners. Safety valves 100 in accordance with the present invention are used to protect the milker units 34 and downstream milk lines from contamination by teat dip fluids during the milking process.

Figure 3A:
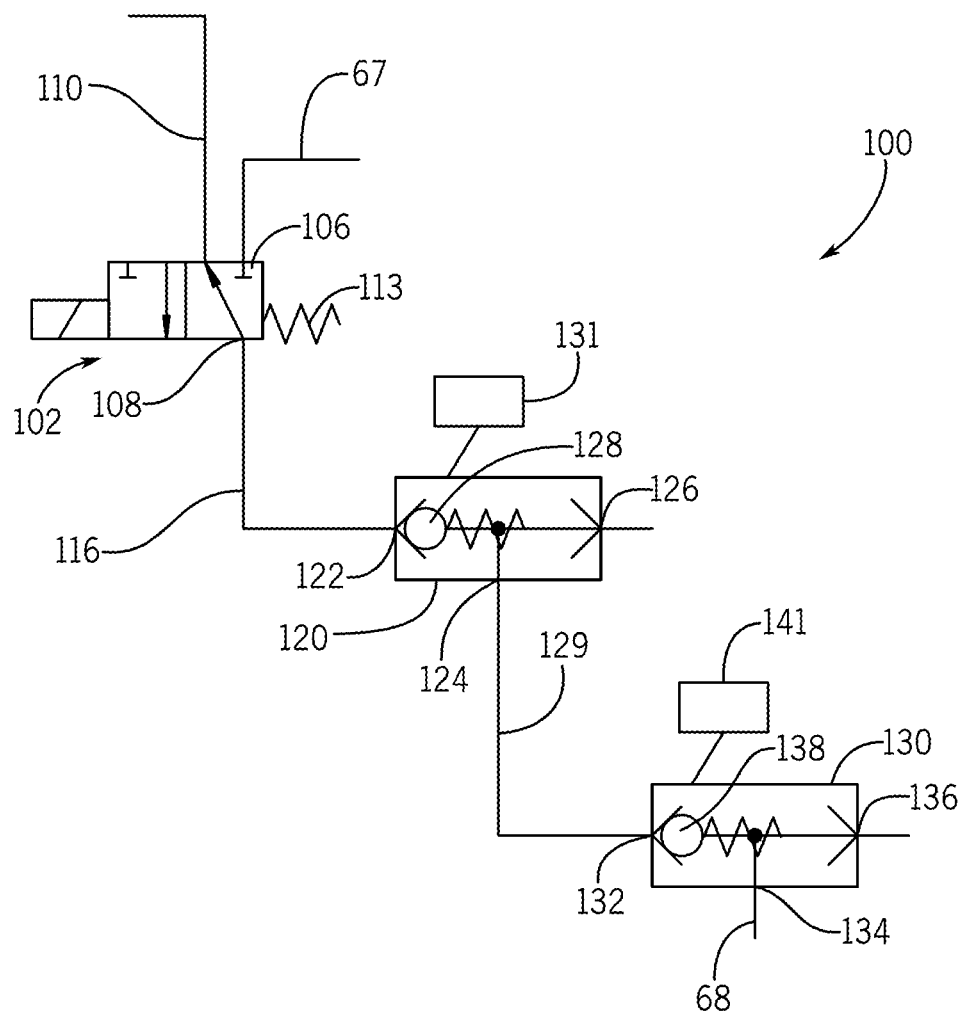
FIG. 3A is a schematic view of a first embodiment of a safety valve in accordance with the present invention.

FIGS. 3A through 3F depict a first embodiment of a safety valve 100 in accordance with the present invention. FIG. 3A uses different valve schematics than FIGS. 3B through 3F to aid in understanding the invention. The safety valve 100 is actually a combination of valves having an upstream valve 102 that is preferably a 2 position-3 way valve having an inlet 106, an outlet 108, and vent 110. The inlet 106 is in fluid communication with a delivery line 67 from the manifold 50 or 52. The outlet 108 feeds a first conduit 116.

In between the inlet 106 and the outlet 108, is the vent 110, which together form a "block-bleed-block" arrangement to protect downstream milk lines from upstream teat dip fluids. The 2 positon-3 way style valve is desirable, because it preferably uses valve seats on which valve heads bear when in the closed position, as opposed to seals in a spool valve which must slide and can be subject to swelling and seizure after extended exposure to teat dip. Nonetheless, under appropriate circumstances, spool valves and other types of valves can be used. An actuator 113 is used to move the valve 100 between a closed position with the vent 110 open and an open position with the inlet 106 in fluid communication with the outlet 108 and the vent 110 closed. Actuators 113 in accordance with the present invention can be any desired type, including springs, solenoid valves, or other passive, active, automated, or manual actuators.

In the embodiment illustrated in FIG. 3A, the first conduit 116 is in fluid communication with a first shuttle valve 120, which is biased toward a normally closed position with an inlet 122, and outlet 124, and a vent 126. A shuttle 128 moves between a closed position against the inlet 122 and an open position, against the vent (or "bleed") 126.

The bias in the first shuttle valve 120 preferably is set at less than the hydraulic or pneumatic pressures of any of the teat dip fluids being dispensed through the safety valve 100, so that the fluid pressure itself is sufficient to actuate or open the first shuttle valve 120 for fluid flow and to close the vent 126 so that fluid does not drain out through the vent 126 while passing downstream. Flow in the opposite direction, (from the outlet 124 and toward the inlet 122) is not possible because the fluid would apply pressure against the shuttle 128 and toward the inlet 122 to maintain the inlet 122 in a closed position. Consequently, any such flow would drain from the shuttle valve 100 through the vent 126 instead of flowing farther upstream.

The position of the shuttle 128 is monitored with a first position sensor 131. Should the valve position sensor 131 sense a shuttle 128 out of position for any given procedure, a corresponding signal can be generated and transmitted to one of the controllers 43 or 44, for example, to further generate a warning and/or stop milking operations at that stall or divert milk to a "bad milk" line, as examples.

The shuttle valve outlet 124 is in fluid communication with a second conduit 129, which in turn is in fluid communication with a second shuttle valve 130 having an inlet 132, an outlet 134, and a vent 136. A shuttle 138 moves between a biased closed position to close the inlet 132 and an open position to open the inlet 132 and close the vent 136. The position of the second shuttle valve 138 is preferably actively monitored by a second position sensor 141, in the same manner described above.

As with the first shuttle valve 120, the second shuttle valve 130 has its bias set at less than the hydraulic or pneumatic pressures of the teat dip fluids, so that only the fluid pressure is necessary to move the second shuttle valve 130 from the closed position to the open position. Also, fluid flow in the opposite direction is not possible because reverse fluid pressure would simply maintain the second shuttle valve 130 in the closed position, and instead the fluid would safely drain out of the vent 136.

With this arrangement of the upstream valve 102, the first shuttle valve 120, and the second shuttle valve 130, one-directional flow through the safety valve 100 is ensured and any possible backflow is safely drained out of the vent 136 and/or the vent 126 (or even the vent 110 in the upstream valve 102) instead of flowing back downstream to the teat cup liner where contamination could occur.

FIGS. 3B through 3F illustrate the safety valve 100 in a progression of valve positions for allowing teat dip fluids to pass toward a teat cup and liner configuration. The valve symbols have been changed slightly from FIG. 3A to better illustrate valve positions.

Figure 3B:
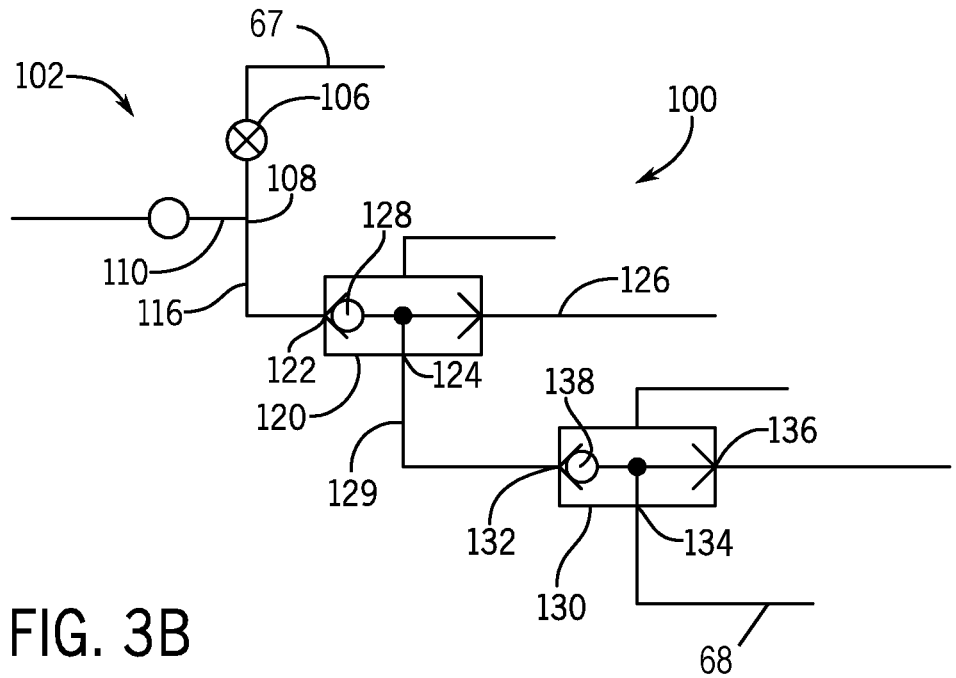
FIG. 3B is a schematic view of the safety valve of FIG. 3A, in a blocked or good milk status.

Beginning with FIG. 3B, the safety valve 100 is closed and in a milking position, so called because downstream milker units and milk lines are protected from upstream teat dipping fluids during the milking process. Specifically, the upstream valve 102 inlet 106 is closed and the vent 110 is opened to provide a block-bleed-block arrangement. In addition, both the first shuttle valve 120 and the second shuttle valve 130 are closed with their respective vents 126 and 136 open to atmospheric pressure. No teat dip fluids can flow through the upstream valve 102, so the shuttle valves 120 and 130 remain closed.

Figure 3C:
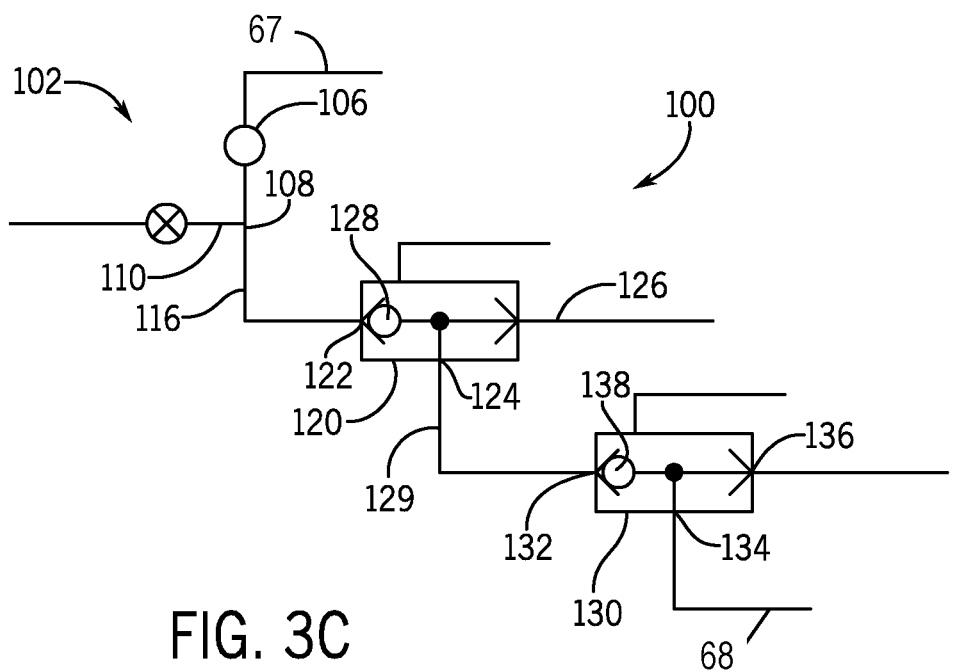
FIG. 3C is a schematic view of the safety valve of FIG. 3A with teat dip passing from a manifold.

After milking, when it is desired to apply teat dip fluids, the safety valve 100 begins to open, as illustrated in FIG. 3C. In this position, the upstream valve 102 now has an open inlet 106, the vent 110 is closed and teat dip fluids can flow from the outlet 110. Nonetheless, teat dip fluid pressure has not yet reached the first shuttle valve 120, so it and the second shuttle valve 130 remain closed.

Figure 3D:
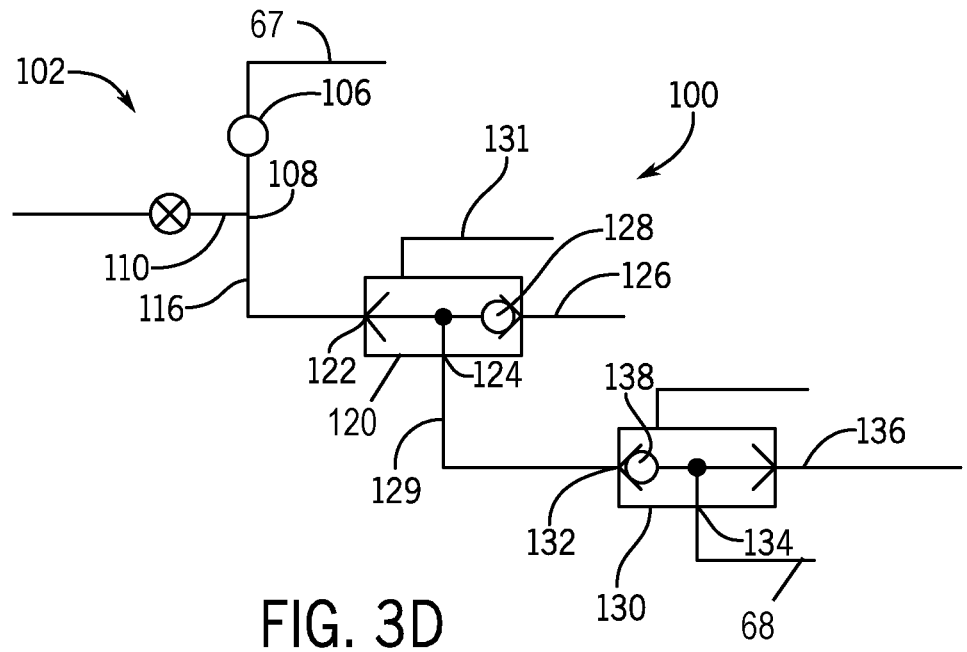
FIG. 3D is a schematic view of the safety valve of FIG. 3A, with dip partially through the safety valve.

As the teat dip fluids pass through the first conduit 116, they eventually reach and open the first shuttle valve 120, as depicted in FIG. 3D. Teat dip fluids have not yet reached the second shuttle valve 130, so it remains closed.

Figure 3E:
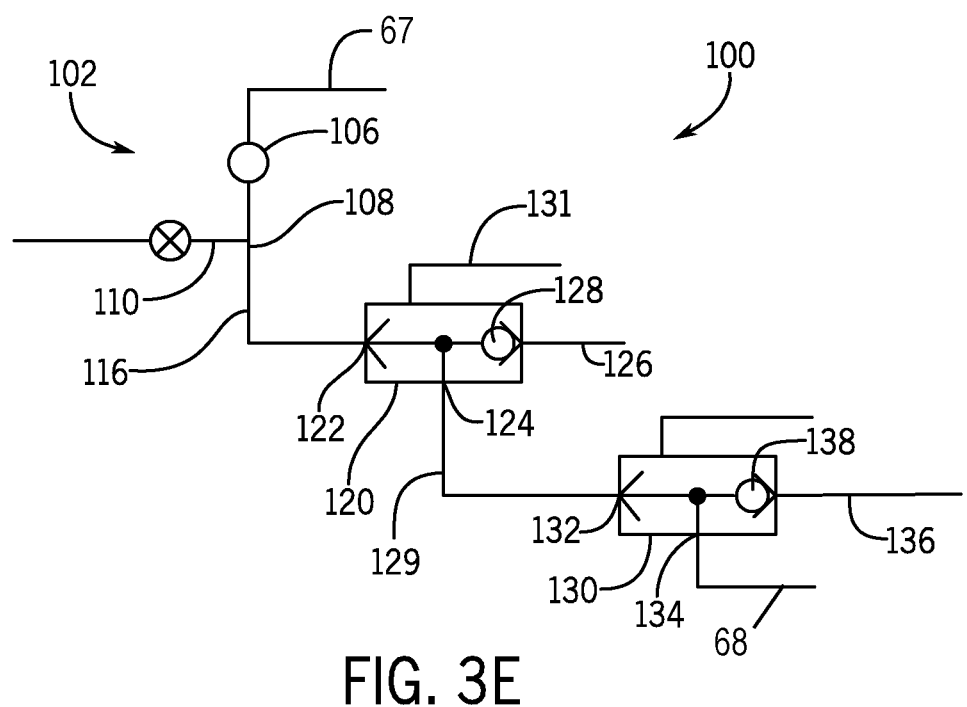
FIG. 3E is a schematic view of the safety valve of FIG. 3A, with dip passing through the safety valve.

FIG. 3E illustrates the second shuttle valve 130 in the open position because teat dip fluid has overtaken the bias of the second shuttle valve 130 and teat dip fluid can flow from the outlet 134 toward a teat cup and liner combination.

After the teat dip fluid has passed through the safety valve 100, additional teat dip fluids can be received from the manifold 50/52, either continuously, or sequentially with any desired intervals in between each teat dip fluid. The teat dip fluids can be related to a pre-dip teat dip fluid or a post-dip teat dip fluid. Operation of the safety valve 100 will be essentially the same for all fluids.

Figure 3F:
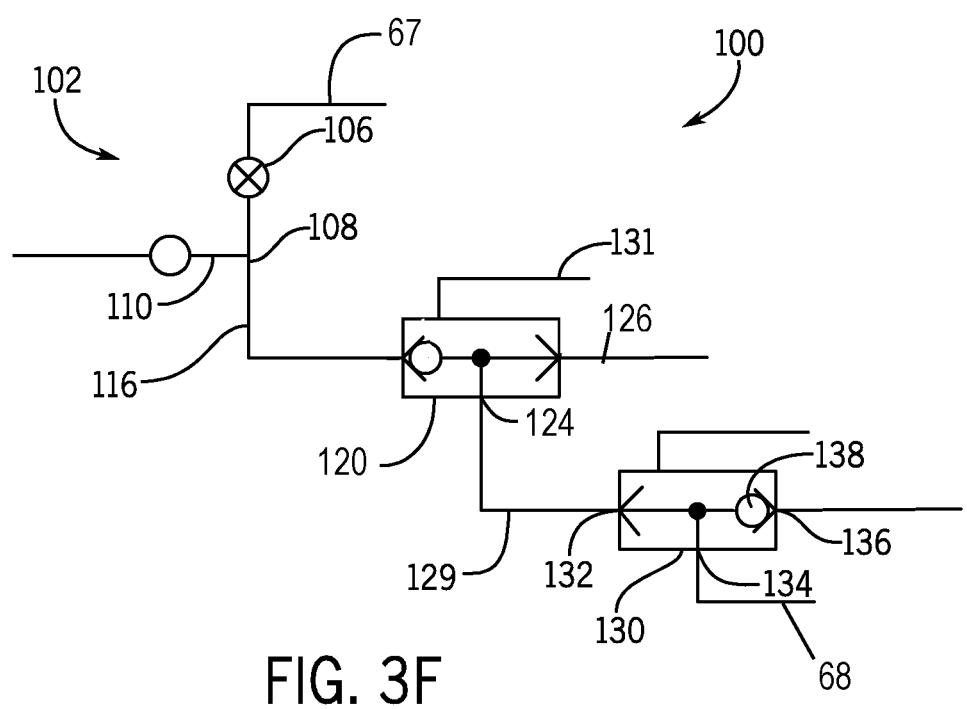
FIG. 3F is a schematic view of the safety valve of FIG. 3A closing down as dip passes through the safety valve.

After completion of the teat dip application and any desired rinsing, the safety valve 100 returns to the milking position by closing the upstream valve 102 to prevent the flow of teat dip fluids. As a result, the first shuttle valve 120 closes first, as seen in FIG. 3F. The second shuttle valve 130 remains open (FIG. 3F) until all of the fluid has passed through the safety valve 100, as illustrated in FIG. 3B, and then closes.

Figure 4:
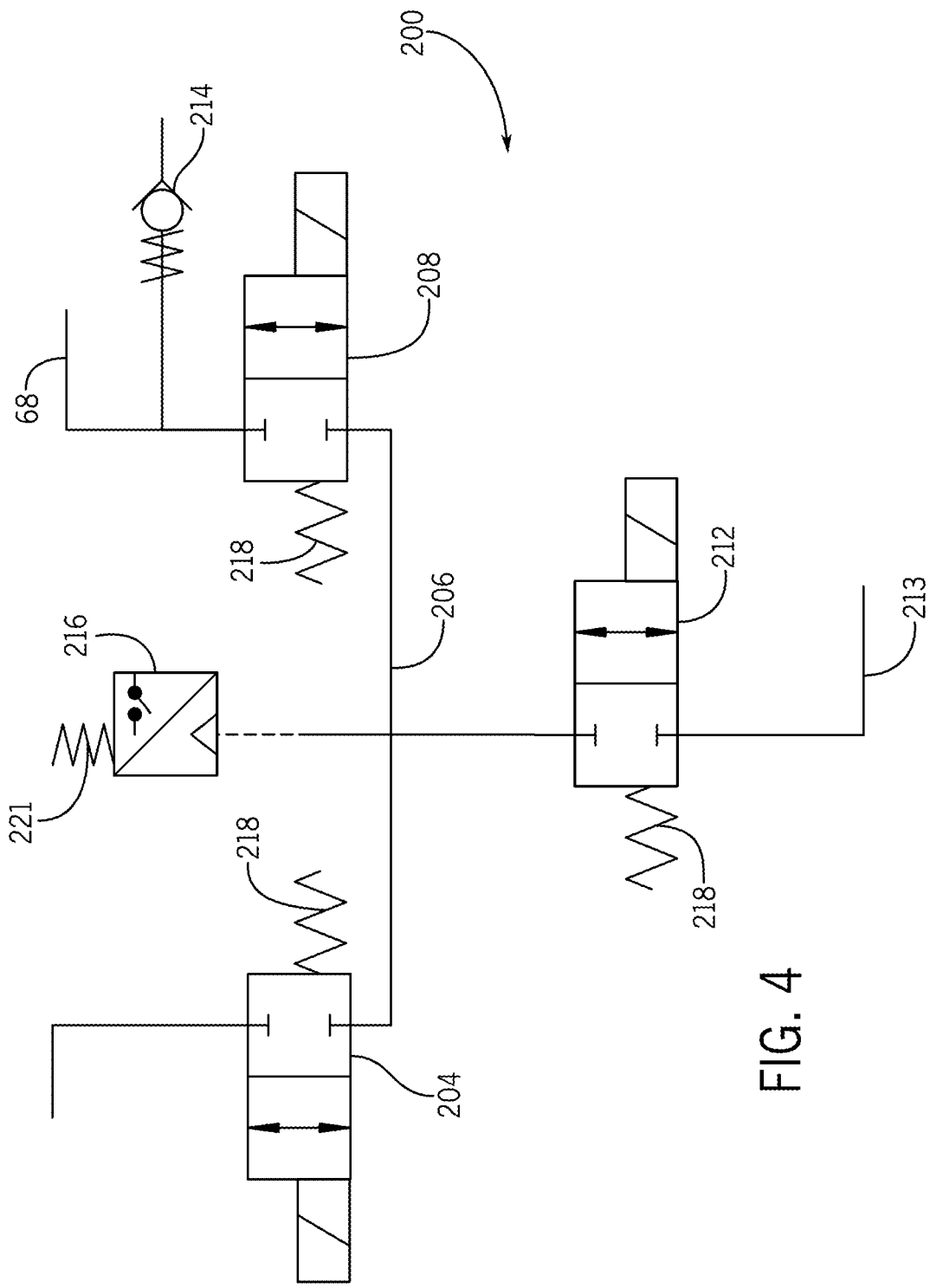
FIG. 4 is a schematic view of a second embodiment of safety valve in accordance with the present invention.

FIG. 4 illustrates a second embodiment of a safety valve 200 in accordance with the present invention, which includes an upstream valve 204, a galley 206, a downstream valve 208, a pneumatic pressure valve 212 in communication with the galley 206, and a pressure monitor 216 also in fluid communication with the galley 206. A vent check valve 214 is also provided to ventilate the galley 206 before or simultaneously with teat dip flowing into the safety valve galley 206, so that the dip pressure does not have to be greater than the galley pressure. In place of the vent 214, or in addition thereto, a vacuum can be applied to the galley 206 to evacuate any pressure and to draw fluid into and through the safety valve 200.

The upstream valve 204, the downstream valve 208, and the pneumatic pressure valve 212 are preferably all normally closed, 2 positon-2 way valves, which are relatively inexpensive to maintain and avoid the use of spools and related seals that can swell and even seize up after prolonged exposure to teat dips. Nonetheless, other valve types can be used, including 2 position-3 way valves, which can be easier to flush and less likely to be fouled by teat dip because they permit rinsing fluids to reach enclosed portions of a fluid flow path.

All of these valves 204, 208, and 212 are controlled by actuators 218. As stated above, "actuators" is used herein to designate any type of valve actuator, including manual and automated, such as a solenoid valve. Preferably, the actuators 218 used with this invention are automated and remotely controlled by the controller 43.

Teat dip fluids flow from the teat dip fluid manifold 50/52 and the dip supply line 67, and into the upstream valve 204, through the galley 206, and out of the downstream valve 208 when the upstream valve 204 and the downstream valve 208 have been actuated into an open position. After these valves 204/208 close, the pneumatic pressure valve 212 opens briefly to permit pressurized gas from a supply line 213, preferably air but other fluids, gases, and vapors could be used, to enter the galley 206 until the galley 206 pressure reaches a predetermined level, preferably about 80 pounds per square inch ("psi"), but other pressures can be used as well. When desired galley 206 pressure is reached, the pneumatic valve 212 closes. With all these valves 204, 208, and 218 closed, pressure in the galley 206 should remain relatively constant unless there is a leak in one of the valves.

A leak would be detectable by the pressure monitor 216, which can be a pressure switch or any other type of pressure gauge or monitoring device that monitors a predetermined pressure or pressure range. A falling pressure or a fluctuating pressure that is above or below a predetermined value range can be used that indicates that the pressurized gas is leaking out one of the valves 204 or 208 or another location. Pressure drop rates could also be detected to indicate the magnitude of the leak, which is beneficial in determining a corrective course of action.

An abnormal galley pressure would cause the pressure monitor 216 to generate and transmit a signal either wirelessly or through an appropriate hard wire connector 221 to any suitable device that would alert a dairy operator that valve maintenance is required. Such "active" monitoring provides improved monitoring capabilities over a "passive" block-bleed-block safety valve that simply vents or "bleeds" leaked fluids out of a vent between valves. Thus, the present active safety valve can be referred to as a "block-monitor-block" safety valve for improved monitoring and safety.

One additional benefit of using pressurized gas in the galley 206, is that if there is a leak, the pressurized gas will seep through a leaky upstream valve 204 in a direction opposite the milk lines, and thus provide improved milk line protection. If the downstream valve 208 is leaking, then only the gas (again preferably air) will reach the milk line and no teat dipping fluids will reach the milk lines. Thus, a pressurized and monitored galley 206 provides excellent milk line protection in an automated dairy milker unit, and can be used in any dairy apparatus where milk lines require protection from other fluids.

One further function of a pressure monitor 216 for monitoring the galley 206, can be achieved when milking and dipping operations are not taking place. During these "down" times, the upstream valve 204 and the downstream valve 208 can be closed, and the pneumatic valve 212 can be opened. If the pressure monitor 216 is unable to detect an adequate or predetermined pressure range, it would indicate that the pneumatic valve 212 or a source for pressurized air is not functioning properly.

Thus, all of the embodiments of the present invention can be used to: monitor galley pressure and determine if there are leaky valves; help maintain upstream valves in a closed position; prevent contaminating fluids from flowing through the safety valve; force air through leaky valves in the opposite direction that contaminating fluids might otherwise flow; and test air pressure sources and the pneumatic pressure valve. Any failures of the safety valve of the present invention in these areas would be detected by the pressure monitor to generate a warning signal that maintenance is necessary and/or that milk being harvested through a failing safety valve should be diverted to a "bad milk" line or "calf milk" line, instead of a "good milk" line.

Figure 5:
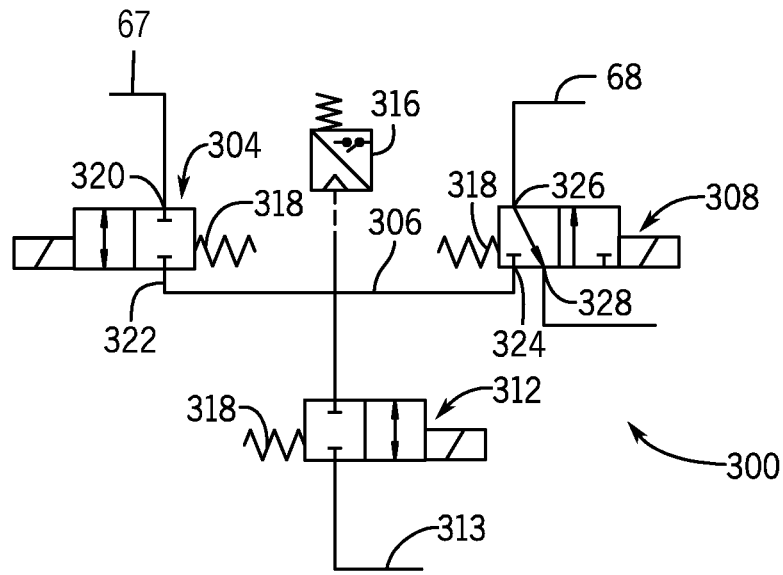
FIG. 5 is a schematic view of a third embodiment of a safety valve in accordance with the present invention.

FIG. 5 illustrates a third embodiment of a safety valve 300 in accordance with the present invention. This safety valve 300 includes an upstream valve 304, a galley 306, a downstream valve 308, a pneumatic pressure valve 312, and a pressure monitor 316, as generally arranged in other embodiments described herein. The galley 306 and all of the galleys of the present invention can be any shape or length, including having tapers and branches that lead to the various valves, but is preferably generally tubular in shape for efficient fluid flow.

In this embodiment the upstream valve 304 is a solenoid-operated 2 way-2 position valve, with an inlet 320 and an outlet 322. The downstream valve 308 is illustrated as a 2 position-3 way valve with an inlet 324 that is normally closed to the galley 306, and an outlet 326 that is normally open to a vent 328 to atmosphere. The pneumatic pressure valve 312 is as described above for other embodiments and receives pressurized gas, such as air, from a source line 313, preferably at a pressure of about 80 pounds per square inch (psi). The valves 304, 308, and 312 are all controlled by actuators 318. The pressure valve 312 allows pressurized gas (air) into the galley 306 when both the upstream valve 304 and the downstream valve 308 are closed. The pressure monitor 316 senses whether the pressure in the galley 306 is within or outside of acceptable ranges, and generates signals, accordingly. This is the arrangement illustrated in FIG. 5.

When teat dip fluids are supplied, both the upstream valve 304 and the downstream valve 308 are opened, and fluids can flow through. Pressurized air from the pressure valve 312 is not supplied at this time so that it does not interfere with fluid flow.

Figure 6:
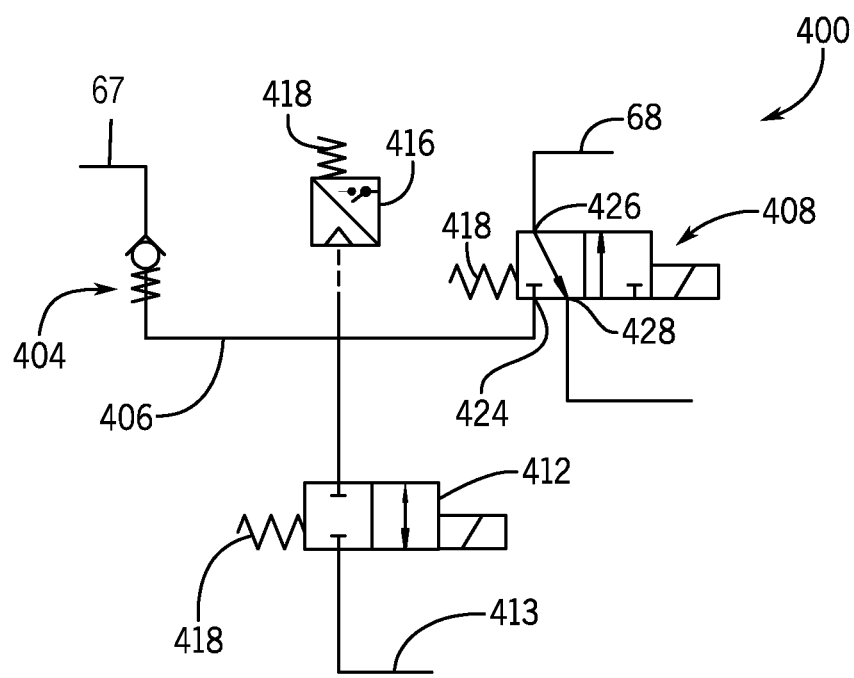
FIG. 6 is a schematic view of a fourth embodiment of a safety valve in accordance with the present invention.
Figure 7:
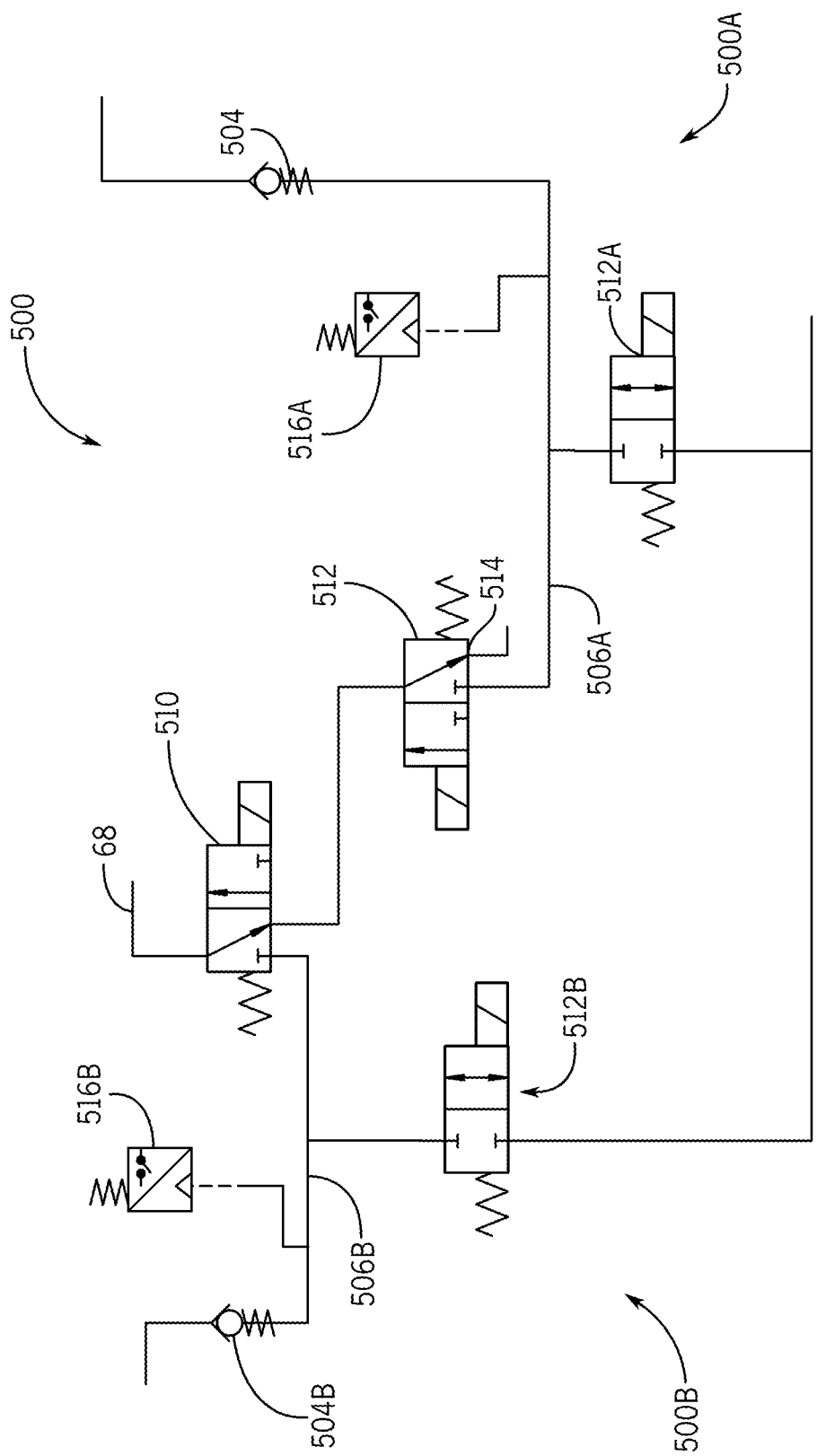
FIG. 7 is a schematic view of a fifth embodiment of a safety valve in accordance with the present invention.

FIG. 6 illustrates a fourth embodiment of a safety valve in accordance with the present invention. This safety valve 400 includes an upstream valve 404, a galley 406, a downstream valve 408, a pneumatic pressure valve 412, and a pressure monitor 416, as generally arranged in other embodiments described herein.

In this embodiment, the upstream valve 404 is preferably a check valve to prevent reverse flow through the safety valve 400. The downstream valve 408 is illustrated as a 2 position-3 way valve with an inlet 424 that is normally closed to the galley 406, and an outlet 426 that is normally open to a vent 428 to atmosphere, so that any reverse fluid flow will drain through the vent 428 before it reaches the inlet 424. The upstream valve 404 is a check valve opened by fluid pressure, but only when dip fluids are supplied by the manifold 50/52. The downstream valve 408 acts as an active block to any downstream flow through the safety valve 400. The pneumatic pressure valve 412 is as described above for other embodiments, and receives pressurized gas, such as air, from a source line 413, preferably at a pressure of about 80 pounds per square inch (psi) to pressurize the galley 406 when the downstream valve 408 is closed and no fluid is opening the upstream valve 404. The pressure sensor 416 acts as described above.

FIGS. 7, and 8A through 8C illustrate a progression of valve positions as teat dip fluids controlled by the pre-dip safety valve 500A, and the post-dip safety valve 500B, as used as a combination. In these illustrations, some of the valves are depicted differently for illustrative purposes, as described below.

Figure 8A:
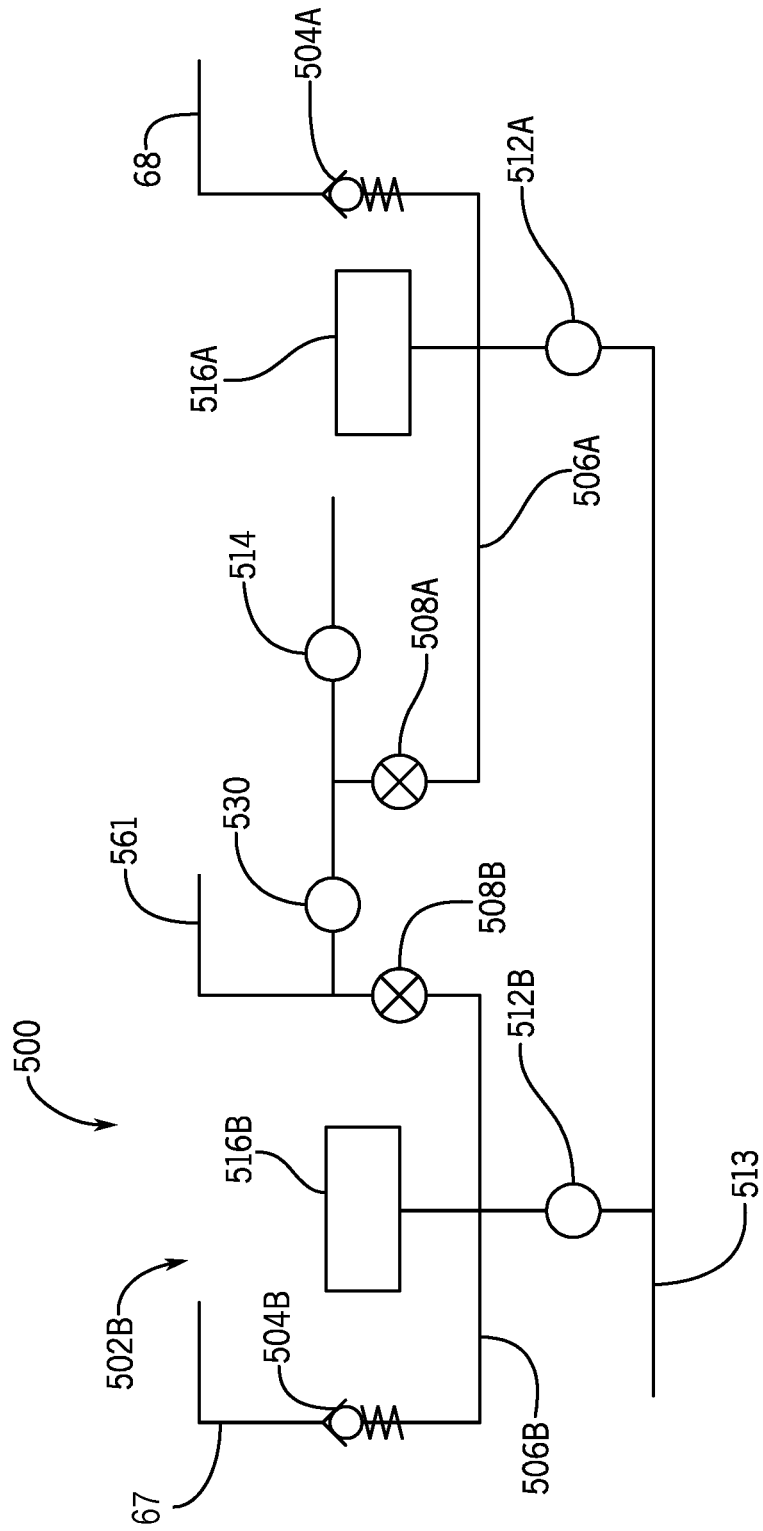
FIG. 8A is a schematic view of the safety valve of FIG. 7 in a blocked or milking position.

For example, in the initial position illustrated in FIG. 8A, the pre-dip safety valve 500A (right side) and the post-dip safety valve 500B (left side) are both closed to the milking system, and this can be referred to as a milking position for the safety valves 500A and 500B to prevent pre and post teat dipping fluids from reaching the milking lines downstream.

Specifically, the inlet valves 504A and 504B (illustrated as check valves) are closed, the outlet valves 508A and 508B are closed, the pneumatic valves 512A and 512B are open to allow pressurized air from gas supply line 513 into the respective galleys 506A and 506B (preferably at about 80 pounds per square inch "psi"), which are monitored by pressure monitors 516A and 516B, respectively. The ventilation valves (or port in a valve) 514 and 530 are opened to provide vents or bleeds in this block-bleed-block arrangement.

Figure 8B:
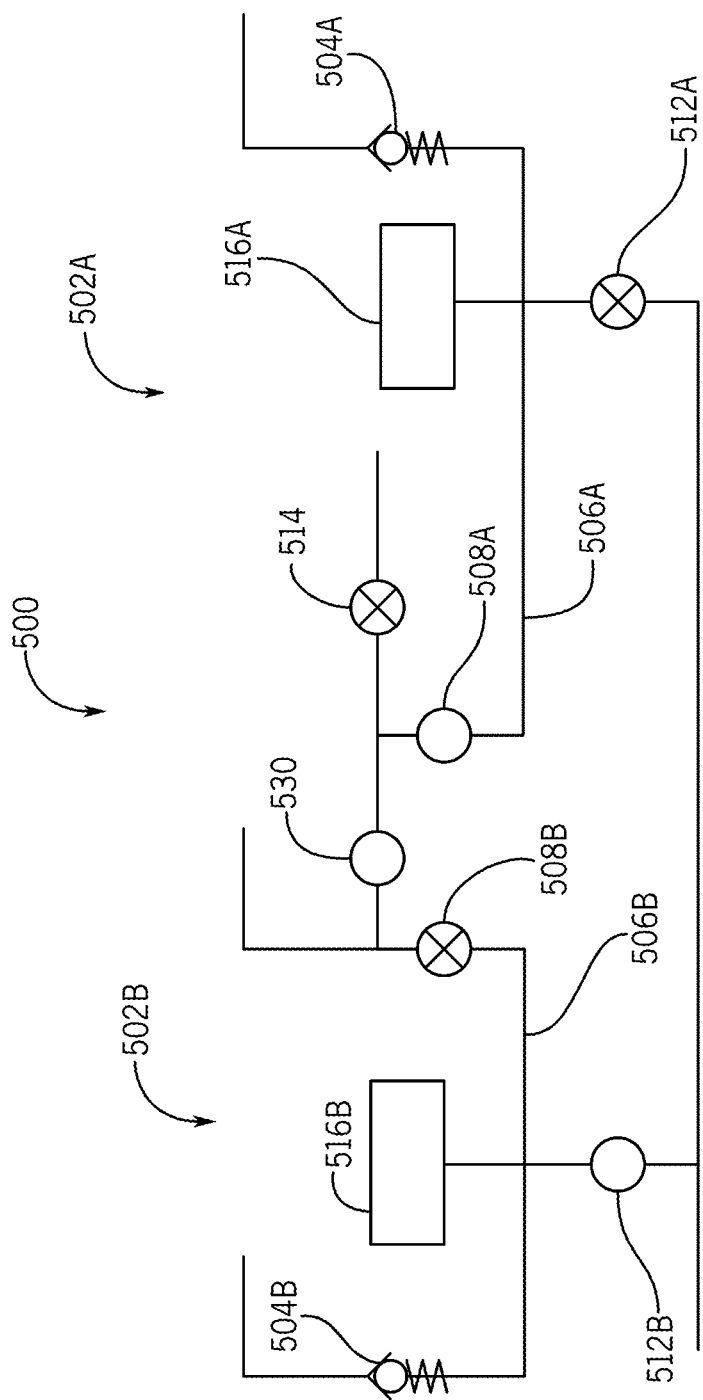
FIG. 8B is a schematic view of the safety valve of FIG. 7 in a pre-dip process position.

FIG. 8B shows the next step in a teat dipping progression. In this step, the pre-dip portion 502A (right side) of the safety valve 500 will be activated to apply teat pre-dip. The upstream valve 504A is still closed, and because pre-dip will be applied first, the downstream valve 508A is opened to allow pressurized air to be released from the galley 506 and the pneumatic valve 512A is closed to stop more pressurized air from reaching the galley 506A. The valve 530 is also opened to release pressurized air to atmosphere and thereby allow pre-dip teat dip fluids to enter the galley 506A without resistance from pressurized air being applied to the check valve 504A. The galley 506B remains full of pressurized air being monitored by the pressure sensor 516B. Subsequently, pressurized teat dip fluids will pass through the upstream valve 504A, through the galley 506A, the downstream valve 508A, the valve 530, and to the teat dip applicator downstream.

Figure 8C:
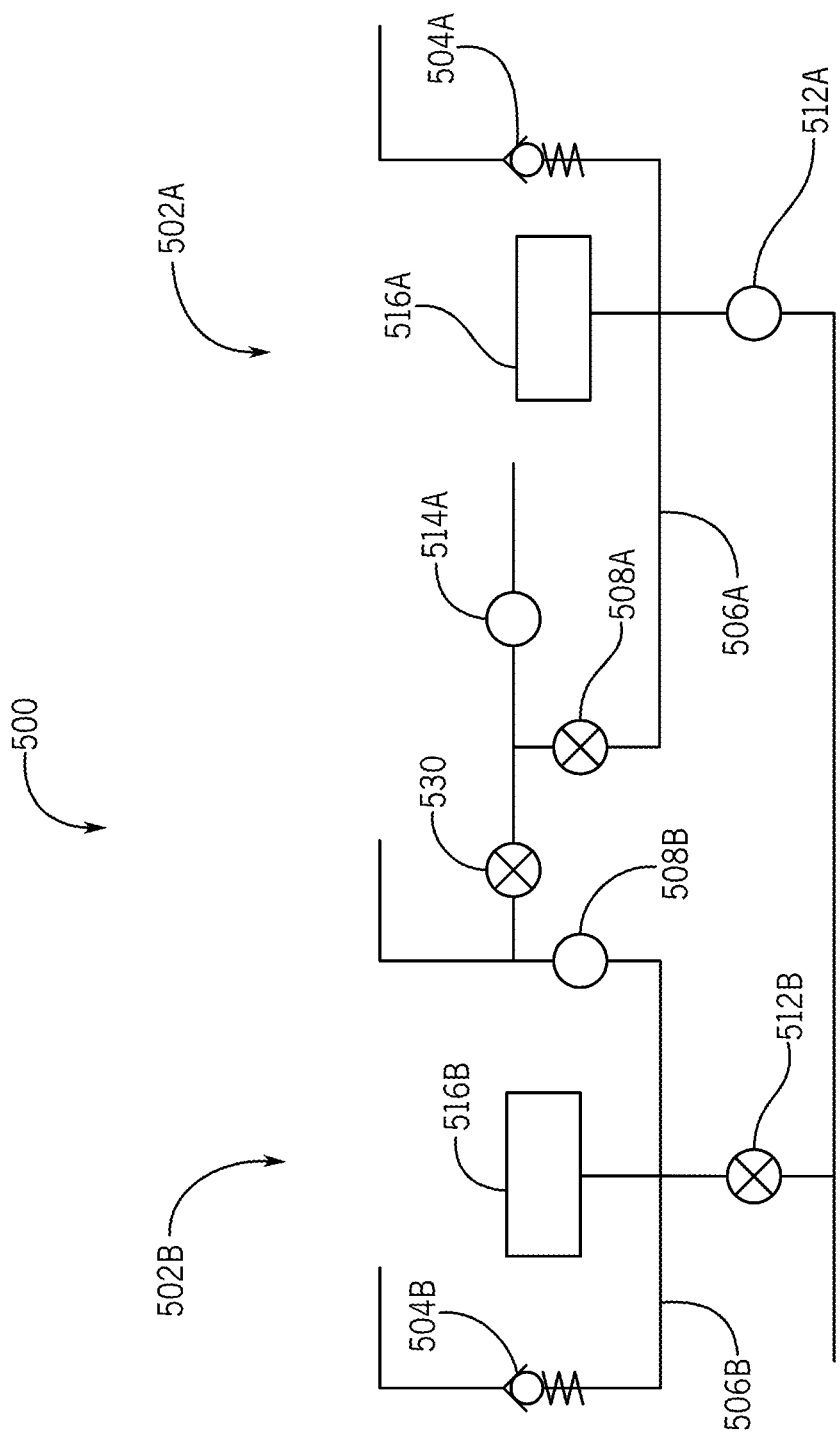
FIG. 8C is a schematic view of the safety valve of FIG. 7 in a post-dip process position.

FIG. 8C illustrates a post-dipping phase of the safety valve 500, in which the post-dip portion 502B (left side) is sequenced. In this phase, the pre-dipping portion 502A is closed down and the galley 506A is filled with pressurized air and being monitored for leaks by the pressure sensor 516A. In addition, the valve 530 is closed to prevent post-dip fluids from entering the pre-dip portion 502A.

On the post-dip portion 502B, the pneumatic valve 512B is closed, the galley 506B is vented out of the downstream valve 508B and post-dipping teat dip fluids can pass through the upstream valve 504B, the galley 506B, the downstream valve 508B and on to the teat dip delivery tube. After post-dipping, the safety valve 500 returns to the valve positions depicted in FIG. 8A.

Figure 9:
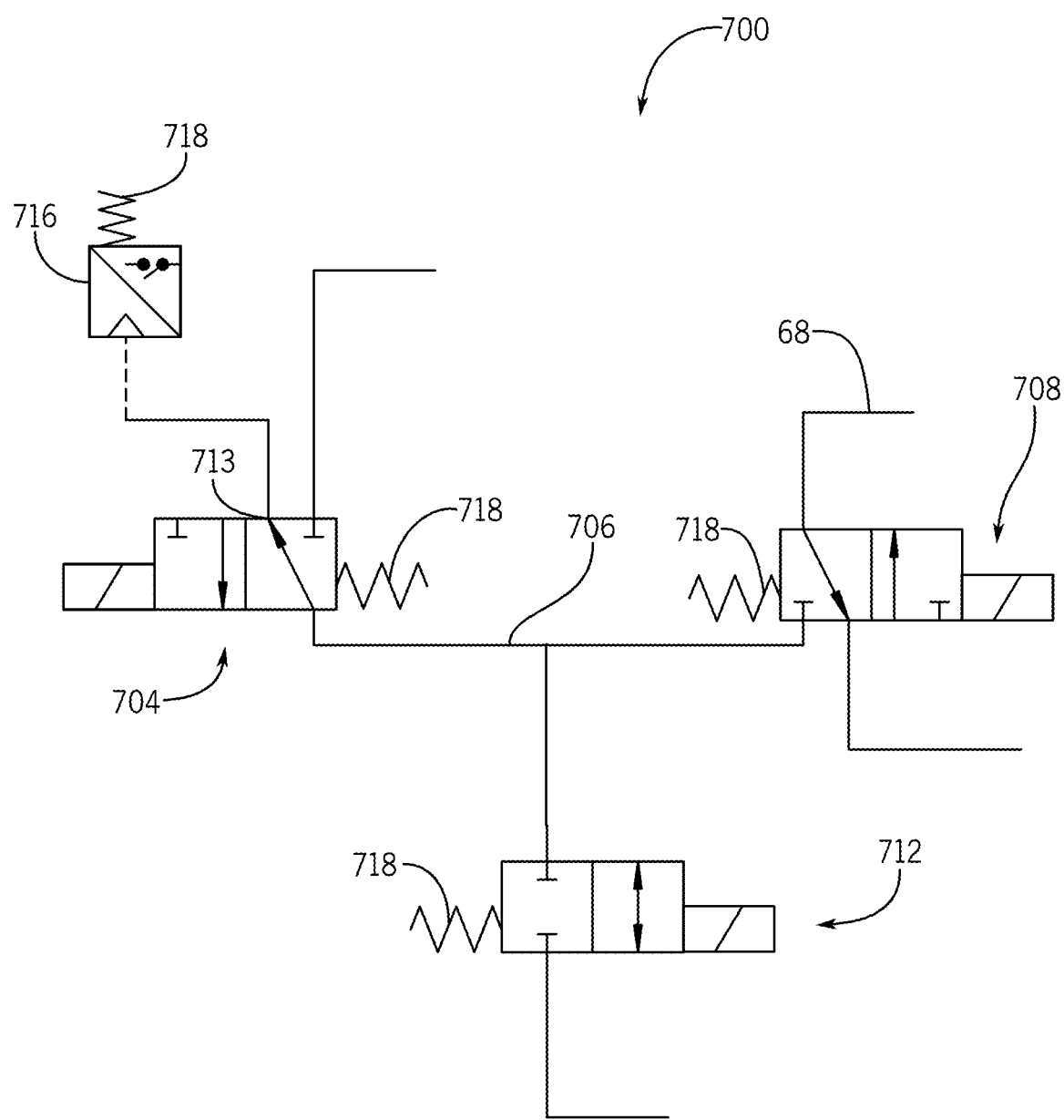
FIG. 9 is a schematic view of a sixth embodiment of a safety valve in accordance with the present invention.

FIG. 9 illustrates another embodiment of a safety valve 700 in accordance with the present invention having an upstream valve 704, a galley 706, a downstream valve 708, and a pneumatic valve 712, all operated by actuators 718 and controlled manually or by a suitable automated controller.

In this FIG. 9 embodiment, the upstream valve 704 is a 2 position-3 way valve used to open or close the safety valve 700, and also defining a galley port 713 when the upstream valve 704 is closed to the dip outlet from a dip manifold 50. The galley port 713 is used to connect a pressure monitor 716 to the galley 706 to monitor galley pressure, as described in the other embodiments above. This arrangement provides protection for the pressure monitor 716 when the upstream valve 704 is closed, so it is not inadvertently contaminated by teat dip fluids.

Figure 10:
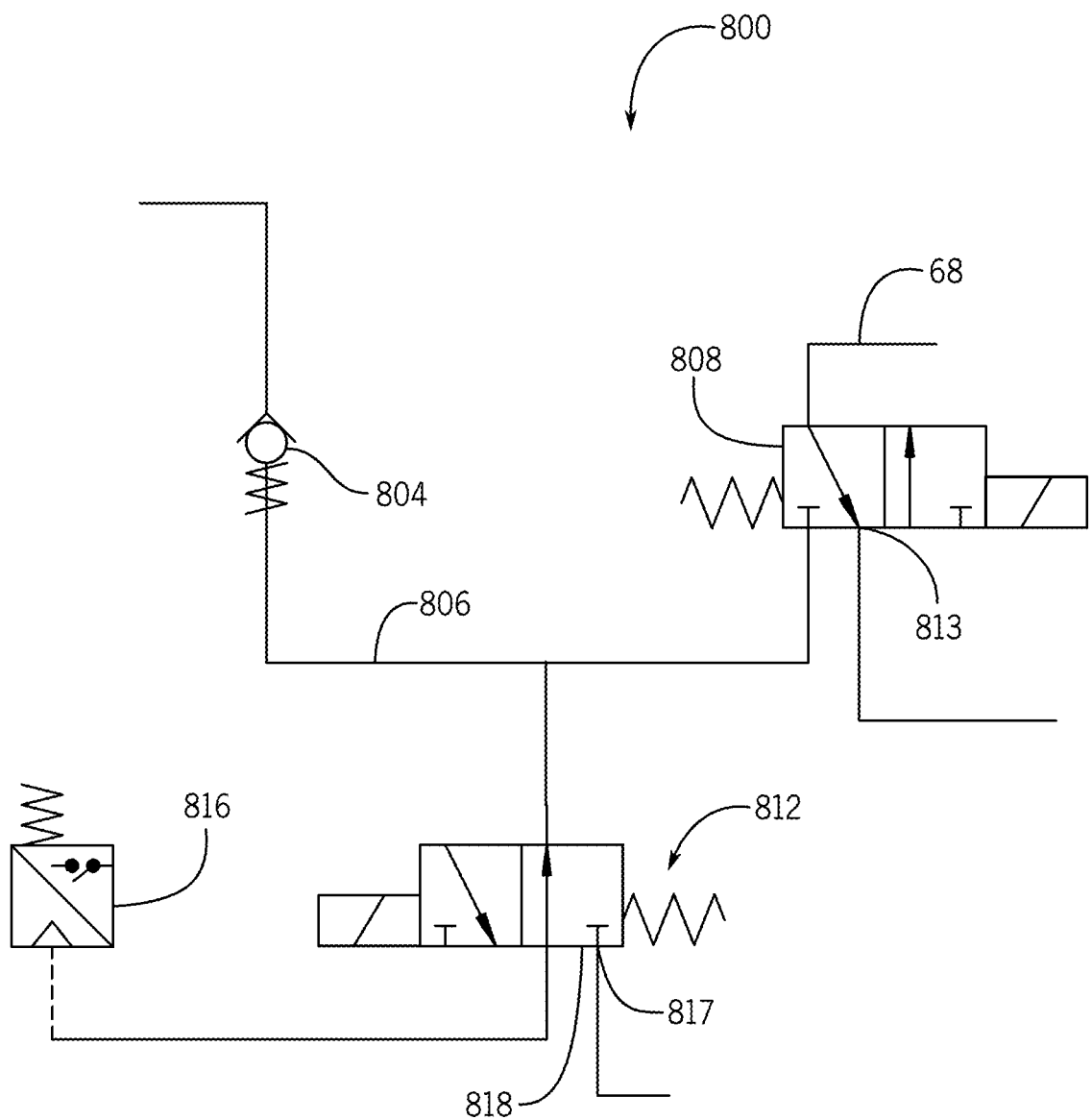
FIG. 10 is a schematic view of a seventh embodiment of a safety valve in accordance with the present invention.

FIG. 10 illustrates another embodiment of a safety valve 800 in accordance with the present invention. This safety valve 800 includes an upstream valve 804, a galley 806, a downstream valve 808, and a pneumatic valve 812.

In this FIG. 10 embodiment, the upstream valve 804 is a check valve, the downstream valve is a 2 positon-3 way valve with a ventilation port 813 opened when the downstream valve 808 is closed to downstream fluid flow. This allows any fluid flowing upstream to drain out of the vent 813 when the downstream valve 808 is closed.

In this embodiment, the pneumatic valve 812 is a 2 positon-3 way valve that defines an inlet 817 for pressurized air, and a monitoring port 818 through which the pressure monitor 816 can monitor galley pressure when the pneumatic valve 812 inlet 817 is closed. This arrangement protects the pressure monitor 816 from damage from other fluids and pressure fluctuations when the pneumatic valve 812 is opened to a pressurized source of air. Otherwise, this safety valve 800 operates as others described herein.

Figure 11:
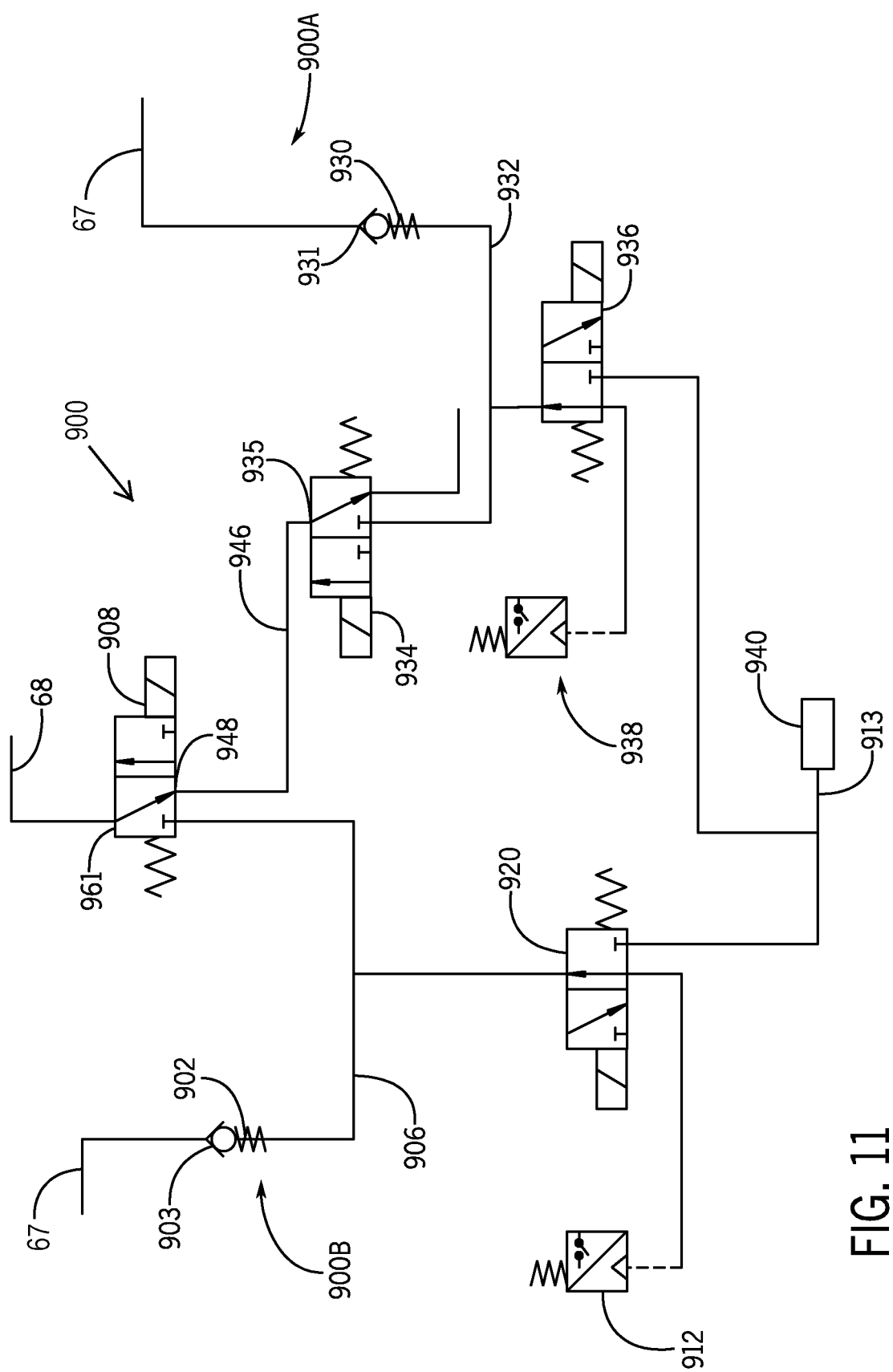
FIG. 11 is a schematic view of an eighth embodiment of a safety valve in accordance with the present invention.

FIG. 11 is an embodiment of a safety valve 900 for use with pre-dip teat dips and post-dip teat dips. In this embodiment, the safety valve 900 is actually two safety valves combined, and with a common outlet 961 for both pre-dips and post-dips. Combining safety valves avoids the use of a blocking pair of check valves to prevent cross contamination. The safety valve 900 preferably dispenses teat dip to a single teat cup, so for a milker unit with four teat cups, four independently operating safety valves 900 will be provided.

In this embodiment, the post-dip teat dipping portion is on the left side of the figure. The dip fluid line 67 leads from the manifold 50/52 to an upstream check valve 902, a galley 906, a downstream valve 908, a pneumatic pressure valve 910, and a pressure monitor 912. The upstream valve 902 and the downstream valve 908, when closed form a pair of blocks separated by the pressurized galley 906 to form a block-monitor-block arrangement in accordance with the present invention, and similar to embodiments described above. Preferably, dip is supplied through the dip fluid line 68 at a maximum of about 60 pounds per square inch (psi), and pressurized air is supplied through the line 913 at about 80 psi, but other relative pressures can be used.

Similarly, the pre-dip dipping portion 900A (right side) includes a dip supply line 67 to an upstream check valve 930, a galley 932, a downstream valve 934, a pneumatic valve 936, and a pressure monitor 938. A source of pressurized air 940 and line 913 are used to pressurize both galleys 906 and 932 when their respective pneumatic valves 910 and 936 are switched to open an appropriate port.

If the post-dip portion 900B and the pre-dip portion 900A of this safety valve 900 were simply connected at their downstream valves 908 and 934, respectively, to a common delivery line 68 downstream of the safety valve 900, then at least a pair of check valves would be required at the outlets 935 and 961 of each downstream valve 908 and 934 to prevent cross contamination of the two halves of the safety valve 900. To avoid including the extra check valves, the present embodiment utilizes a pre-dip outlet tube 946 from the downstream valve 934 of the pre-dip portion and routes it through a port 948 in the downstream valve 908 of the post-dip portion of the safety valve 900. The downstream valve 908 can then be switched to receive pre-dip from the pre-dip outlet tube 946, or switched to receive post-dip from the galley 906 on the post-dip side of the safety valve 900. This downstream valve 908 is preferably a 2 position-3 way valve and, as such, it obviates the need for check valves in protecting the two safety valve portions from cross-contamination.

Figure 12A:
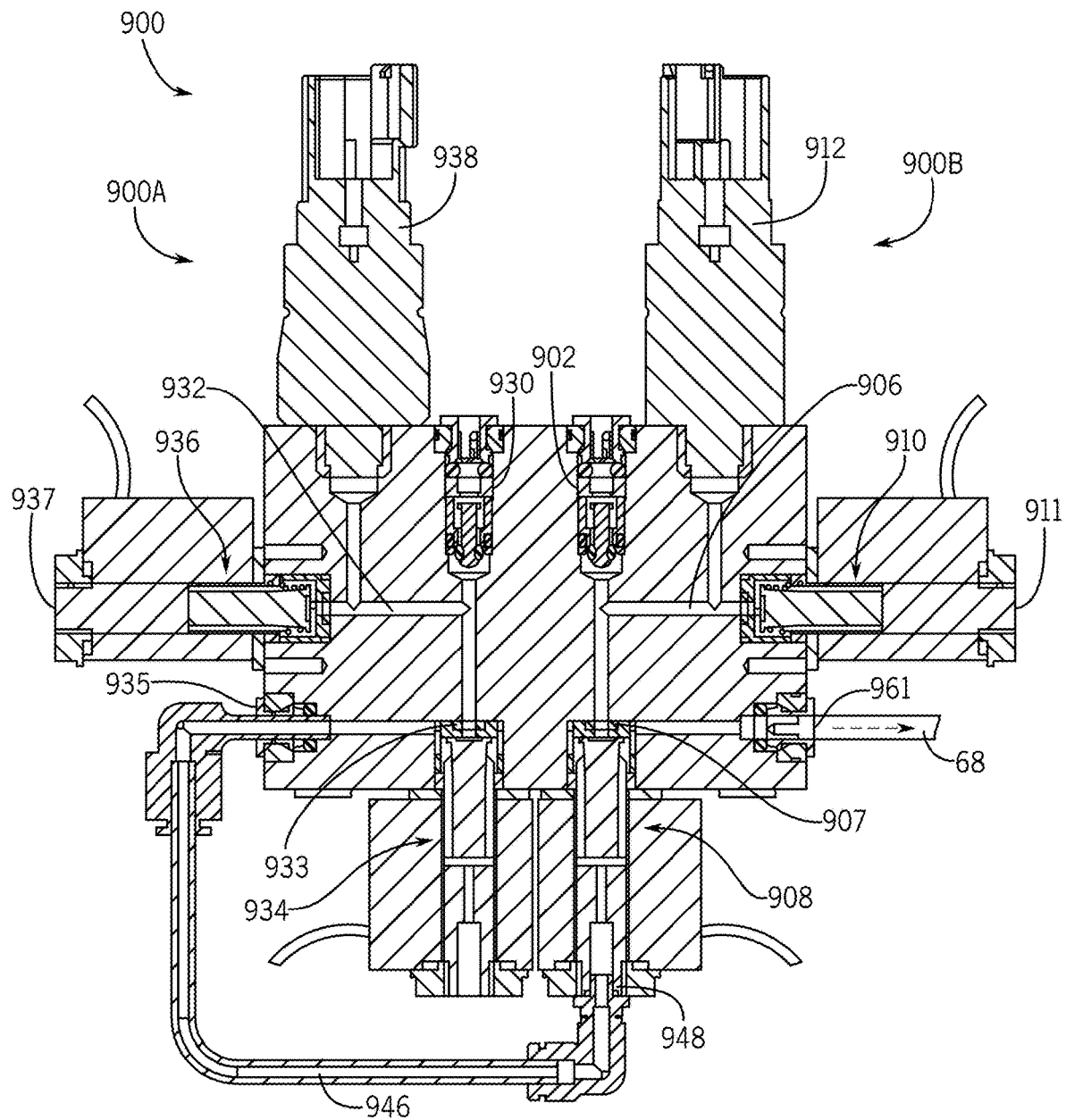
FIG. 12A is a cross sectional view of a safety valve in accordance with the present invention in a "good milk" process state.
Figure 12B:
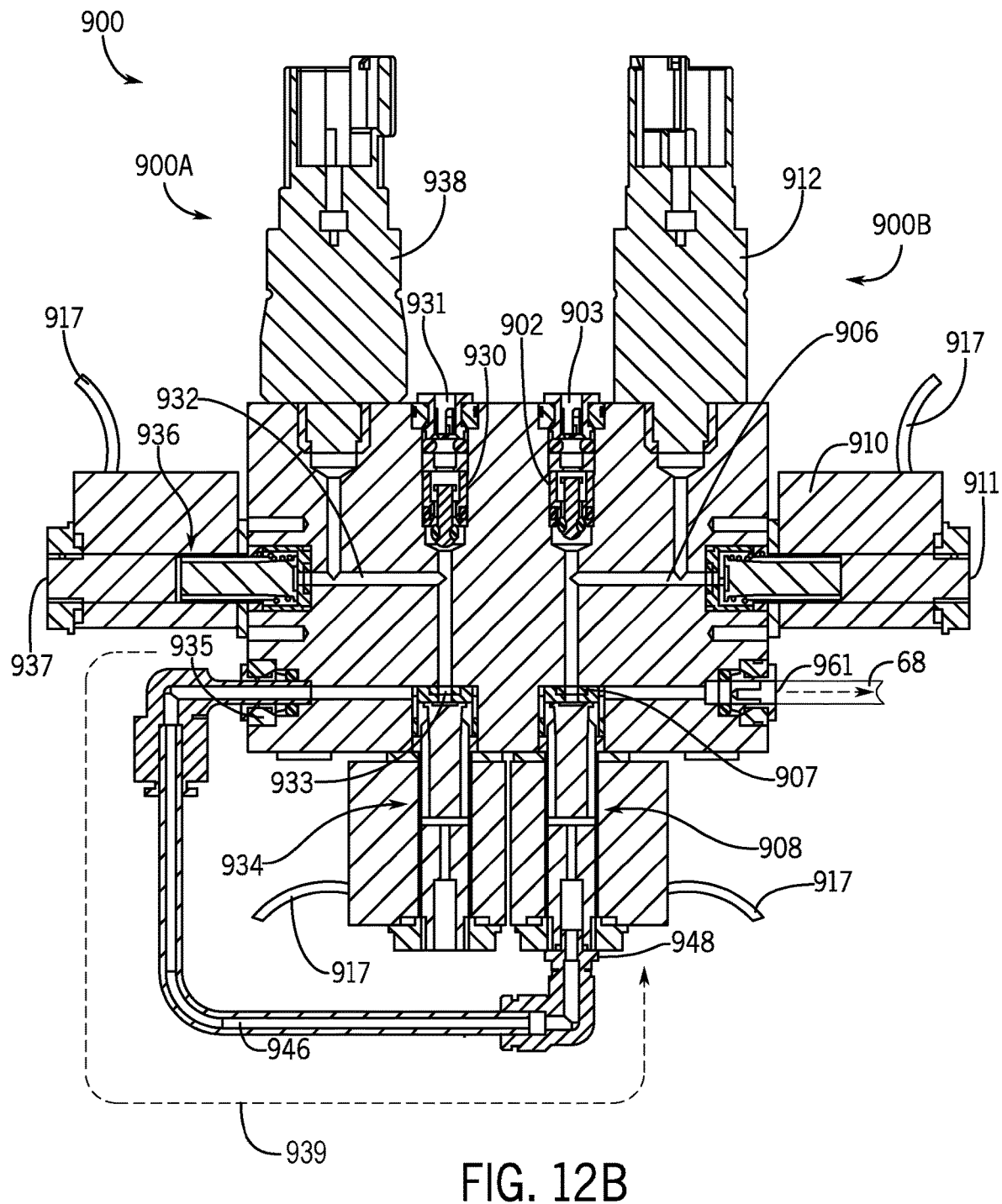
FIG. 12B is a cross sectional view of the safety valve of FIG. 12A, in a pre-dip process state.
Figure 12C:
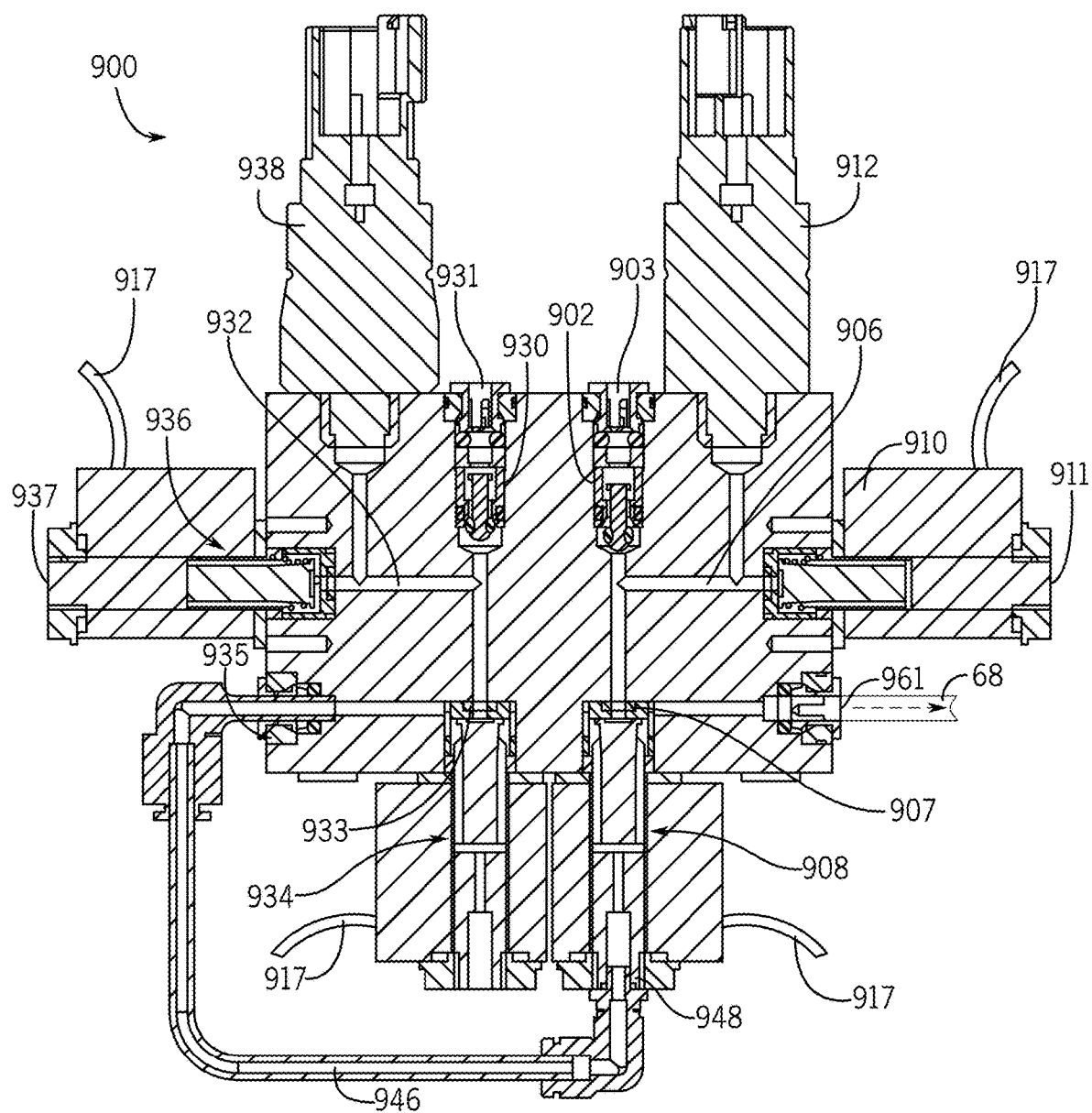
FIG. 12C is a cross sectional view of the safety valve of FIG. 12A in a "post-dip" process state.

As illustrated in FIGS. 12A to 12C, the pre-dip portion 900A is on the left, and the post-dip portion 900B is on the right, which is the opposite orientation from FIG. 11. Therefore, for consistency, starting with the post-dip portion 900B, there is an upstream valve 902, a galley 906, a downstream valve 908, a pneumatic valve 910, and a pressure monitor 912. Preferably, the upstream valve 902 is a check valve, the downstream valve is a 2 position-3 way valve, and the pneumatic valve 910 is a 2 position-2 way valve.

Similarly, on the pre-dip side 900A, the upstream valve 930 preferably is a check valve, the downstream valve 934 is a 2 position-3 way valve, and the pneumatic valve 936 is a 2 position-2 way valve.

Step 1 illustrated in FIG. 12A is a "Good Milk Process State" and in it the upstream valves 902 and 930 are closed, the downstream valves 908 and 934 are closed, and the pneumatic valves 910 and 936 are opened to allow pressurized air from source lines 911 and 937, respectively, into the respective galleys 906 and 932, which are monitored by the respective pressure monitors 912 and 938. In this configuration, the safety valve 900 separates the upstream teat dip fluids from the downstream milk lines with a block-monitor-block arrangement.

In step 2, a "Pre-Dip Process State," as illustrated in FIG. 12B, the upstream pre-dip valve 930 is open, the downstream pre-dip valve 934 is open, and the pneumatic valve 936 is closed. This configuration allows pre-dip to flow through the pre-dip portion 900A of the safety valve 900, but post-dip cannot flow through the safety valve 900 because the post-dip portion 900B upstream valve 902 and downstream valve 908 remain closed, although its pneumatic valve 910 remains open to allow pressurized air to enter the galley 906 for monitoring.

Pre-dip enters the pre-dip upstream valve 930 inlet 931 and through the galley 932 and into the pre-dip downstream valve 934 inlet 933 and out of the pre-dip downstream valve outlet 935. The outlet 935 can have any suitable fittings or couplings necessary to connect downstream components. A dashed line 939 illustrates the flow path of pre-dip. When the pre-dip downstream valve 934 is open, the pre-dip flows through the outlet tube 946 and into the post-dip downstream valve through a secondary inlet 948 in the post-dip downstream valve 908 and then exits a common outlet 961 to delivery line 68. So, even in its "closed" position, pre-dip is able to flow through the second inlet 948 and out of the outlet 961.

In step 3, a "Post-Dip Process State" illustrated in FIG. 12C, the pre-dip upstream valve 930 and downstream valve 934 are closed, and the pneumatic valve 936 is open to pressurize the galley 932 for monitoring by the pressure monitor 938.

On the post-dip side 900B, the upstream check valve 902 is open by pressure from the fluid entering the inlet 903 and flowing through the galley 906 to the open downstream valve 908 inlet 907. The pneumatic pressure valve 910 is closed. Post-dip can, therefore, pass through the post-dip side of the safety valve 900B by flowing into the inlet 903 of the upstream valve 902, the galley 906, and into the opened post-dip inlet 907 and out of the common outlet 961. Thus, the benefits of using a common valve outlet 961 are achieved.

Power to all of the valves is provided in any suitable manner, including wires 917.

Figure 15A:
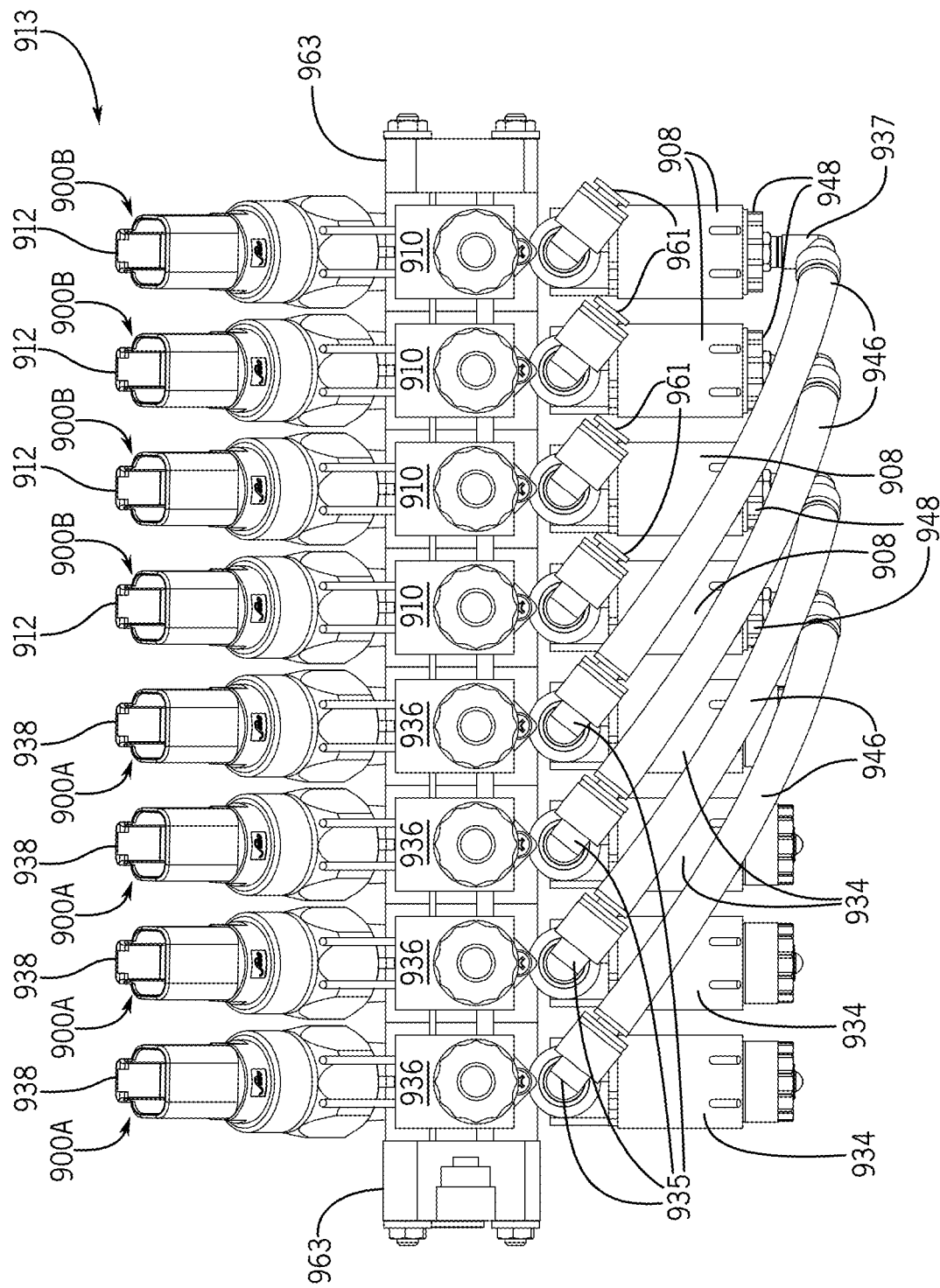
FIG. 15A is a front view of an array of eight safety valves.
Figure 15B:
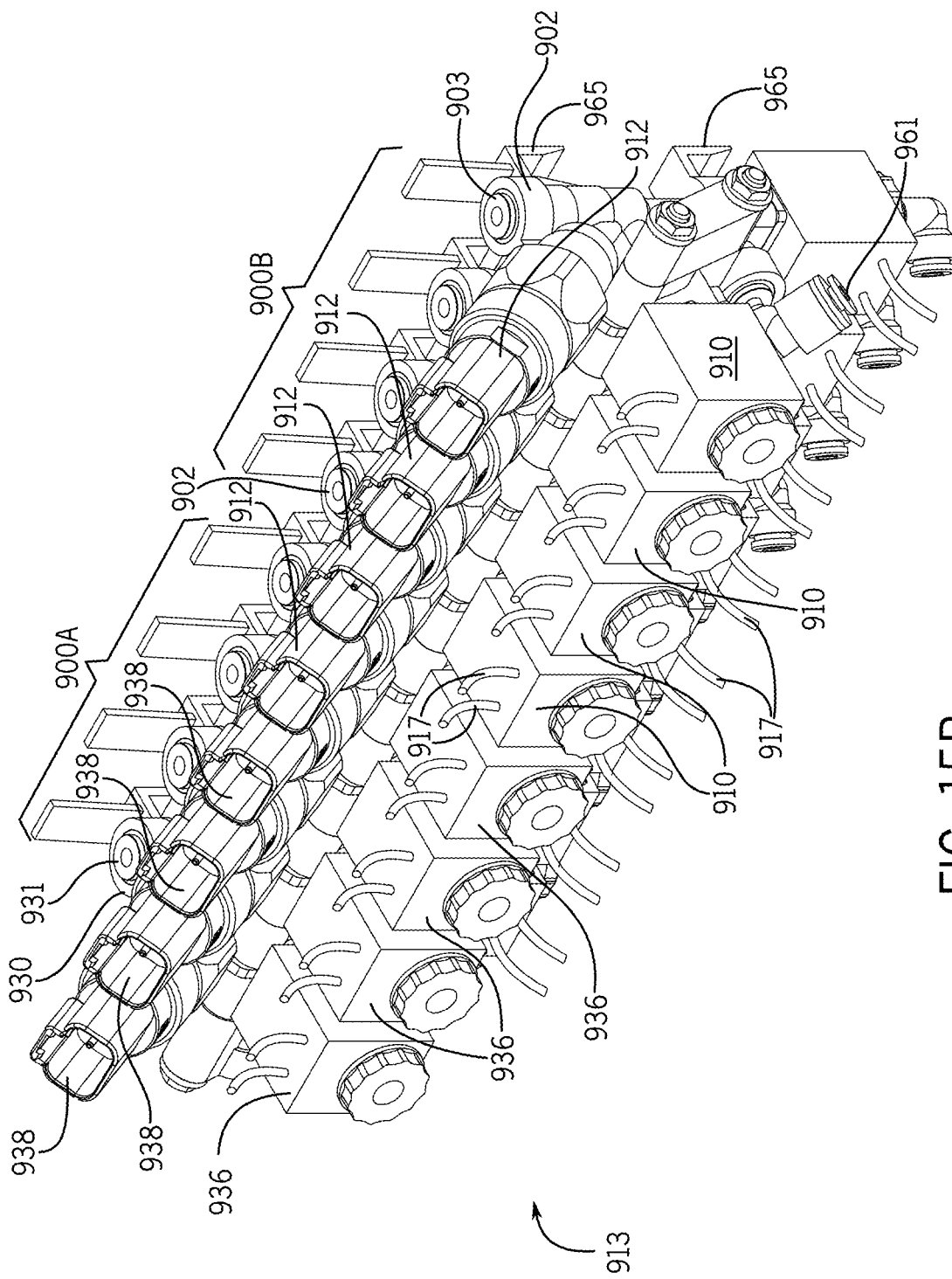
FIG. 15B is a perspective view of the array of eight safety valves of FIG. 15A.

FIGS. 12A through 12C illustrate a progression of cross-sectional views of safety valve 900, similar to the embodiment described above in the schematic FIG. 11. As indicated above, the safety valve 900 is actually a pair of interacting safety valves, with a pre-dip portion 900A and a post-dip portion 900B, which when combined this way provide efficiencies that save space, and avoid unnecessary valves, and tubing. The pre-dip portion 900A and post-dip portion 900B can be arranged in any suitable way, including back-to-back (FIGS. 12A to 12C), side-by-side, an array (FIGS. 15A to 15B), or any other desired arrangement.

Figure 14A:
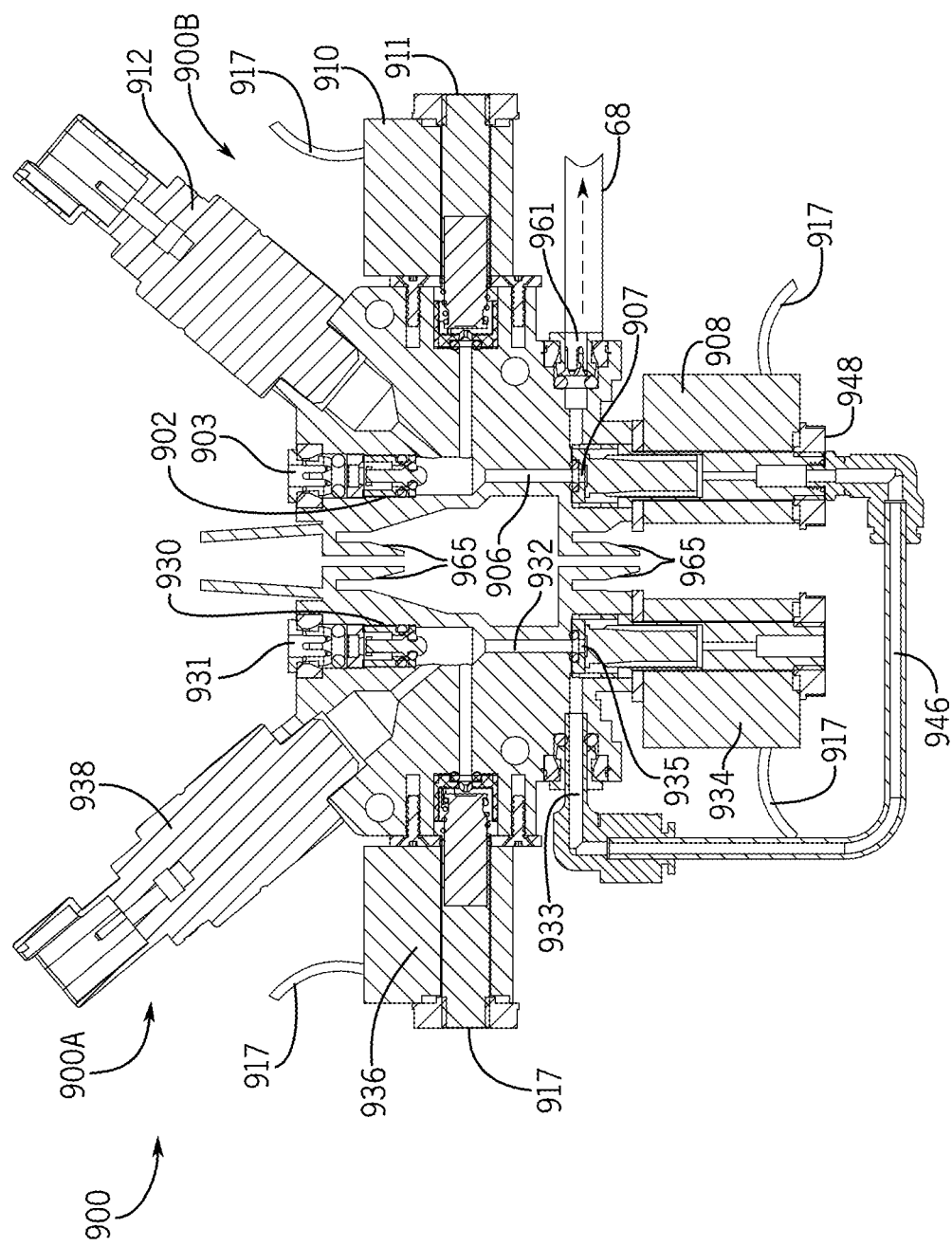
FIG. 14A is a cross sectional view of a safety valve assembly in a "good milk" process state.
Figure 14B:
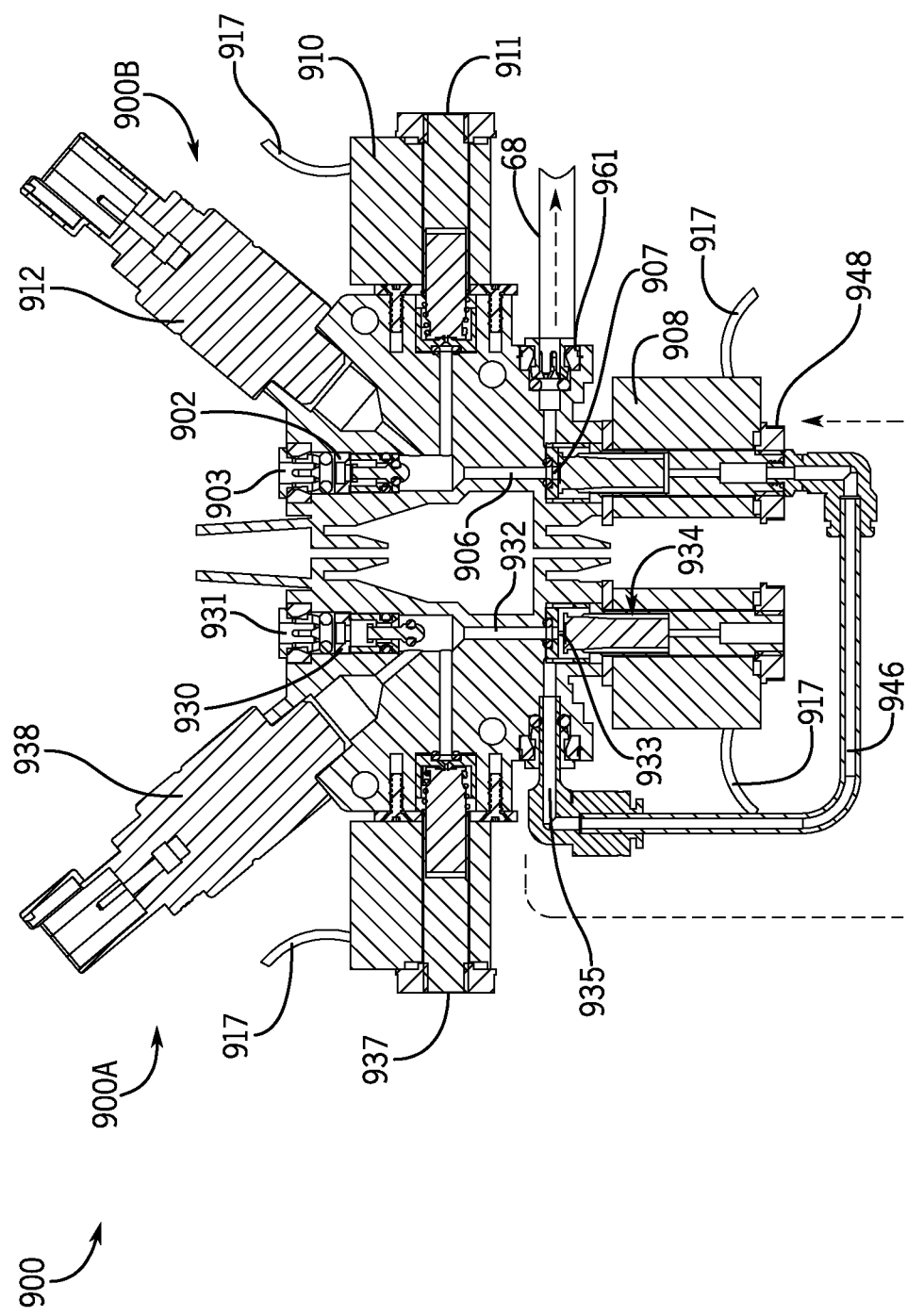
FIG. 14B is a cross sectional view of the safety valve assembly of FIG. 14A in a "pre-dip" process state.
Figure 14C:
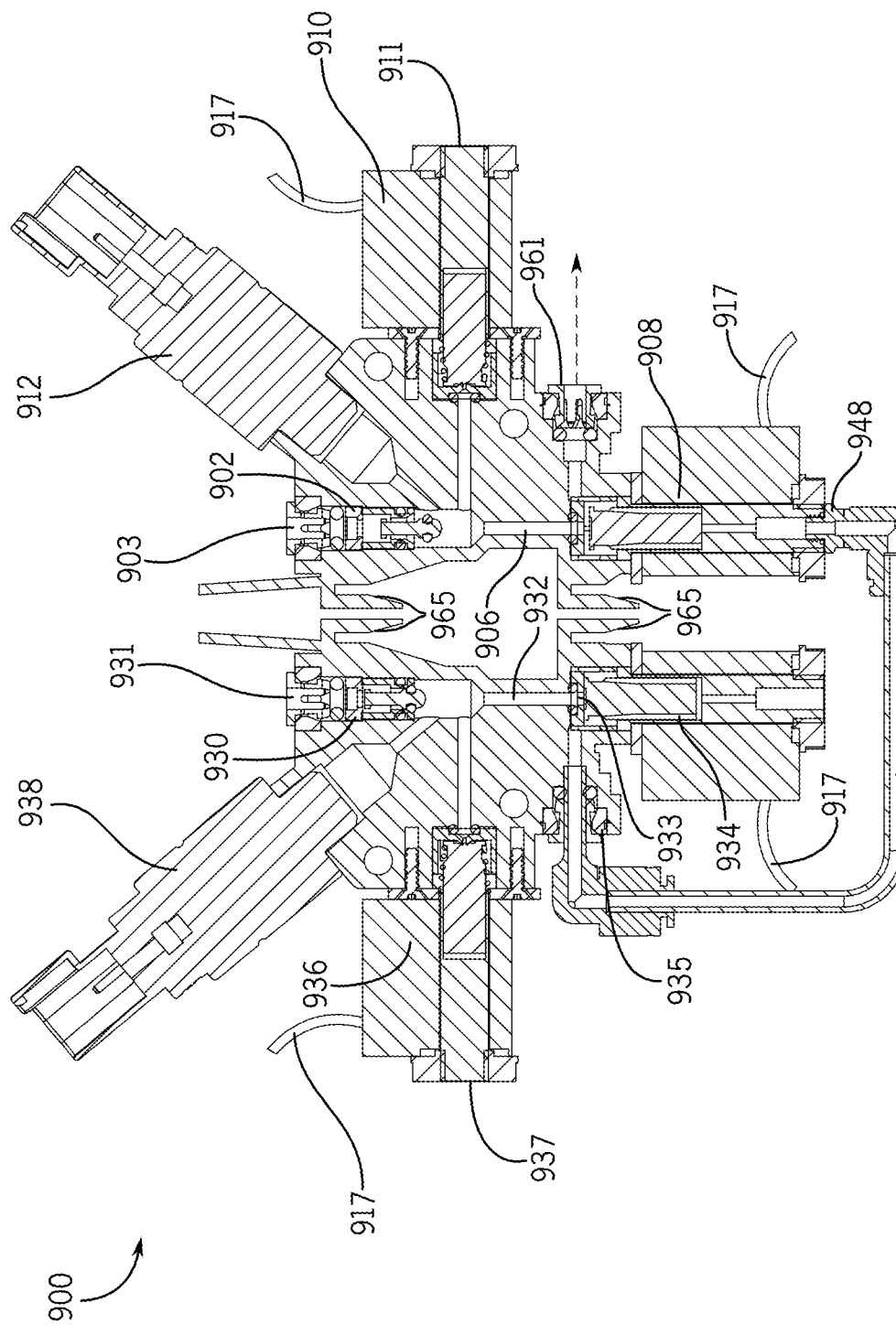
FIG. 14C is a cross sectional view of the safety valve assembly of FIG. 14A in a "post-dip" process state.

FIGS. 14A through 14C illustrate a safety valve that is substantially similar to the embodiment of FIGS. 12A through 12C, except that FIGS. 14A through 14C illustrate the pressure monitors 912 and 938 at angles instead of vertically as in FIGS. 12A through 12C. This arrangement provides improved efficiencies in manufacturing and overall safety valve 900 size. Further, the shapes of the galleys 906 and 938 in FIGS. 14A to 14C provide more efficient fluid flow and junctions with the related valves are open. This embodiment also includes hooks 965 for joining the safety valve portions 900A and 900B to a rack or frame, for example. Otherwise, the operation of the safety valve 900 in FIGS. 14A through 14C is essentially the same as the safety valve 900 of FIGS. 12A through 12C.

Figure 13A:
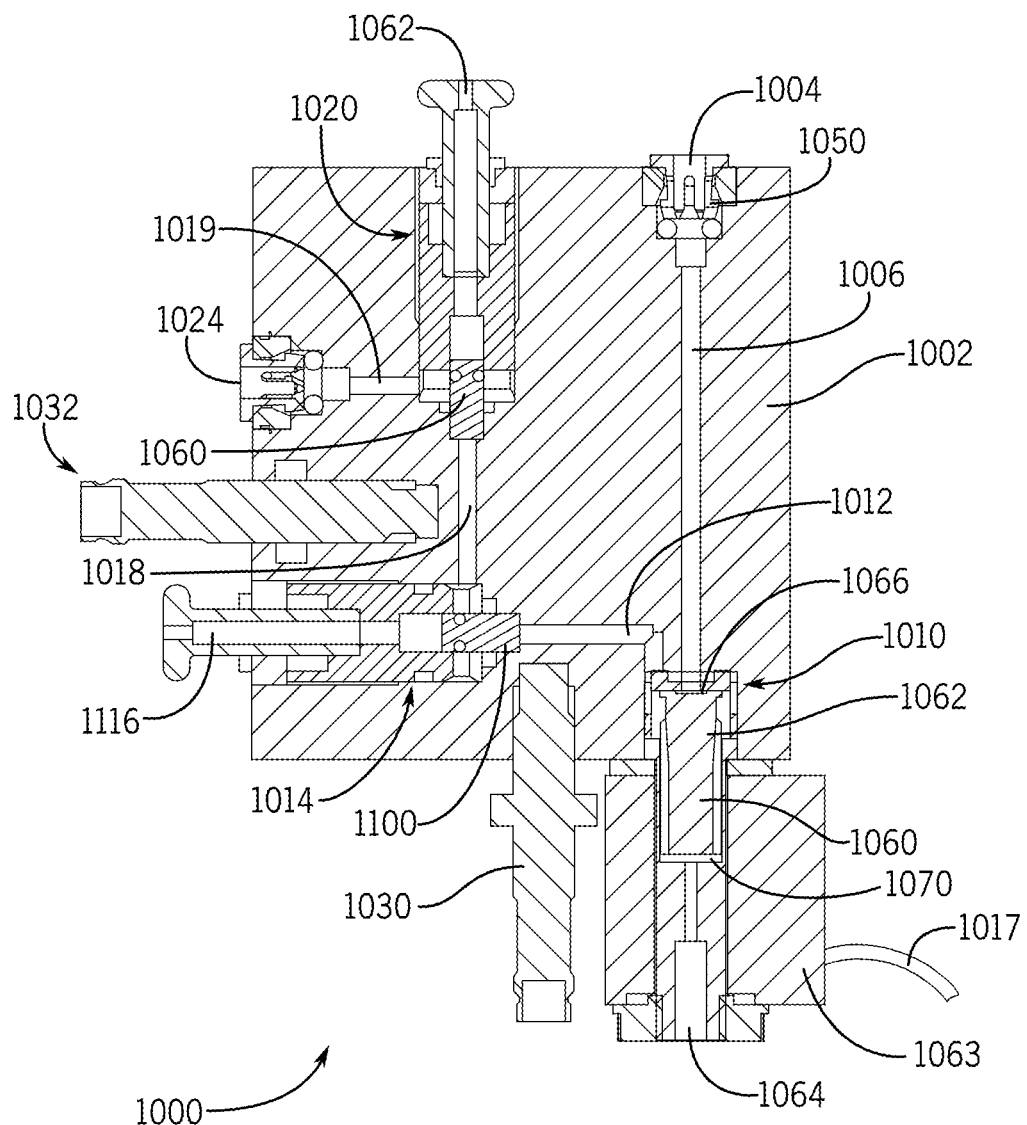
FIG. 13A is a cross sectional view of the safety valve in accordance with the present invention in a "good milk" state.
Figure 13B:
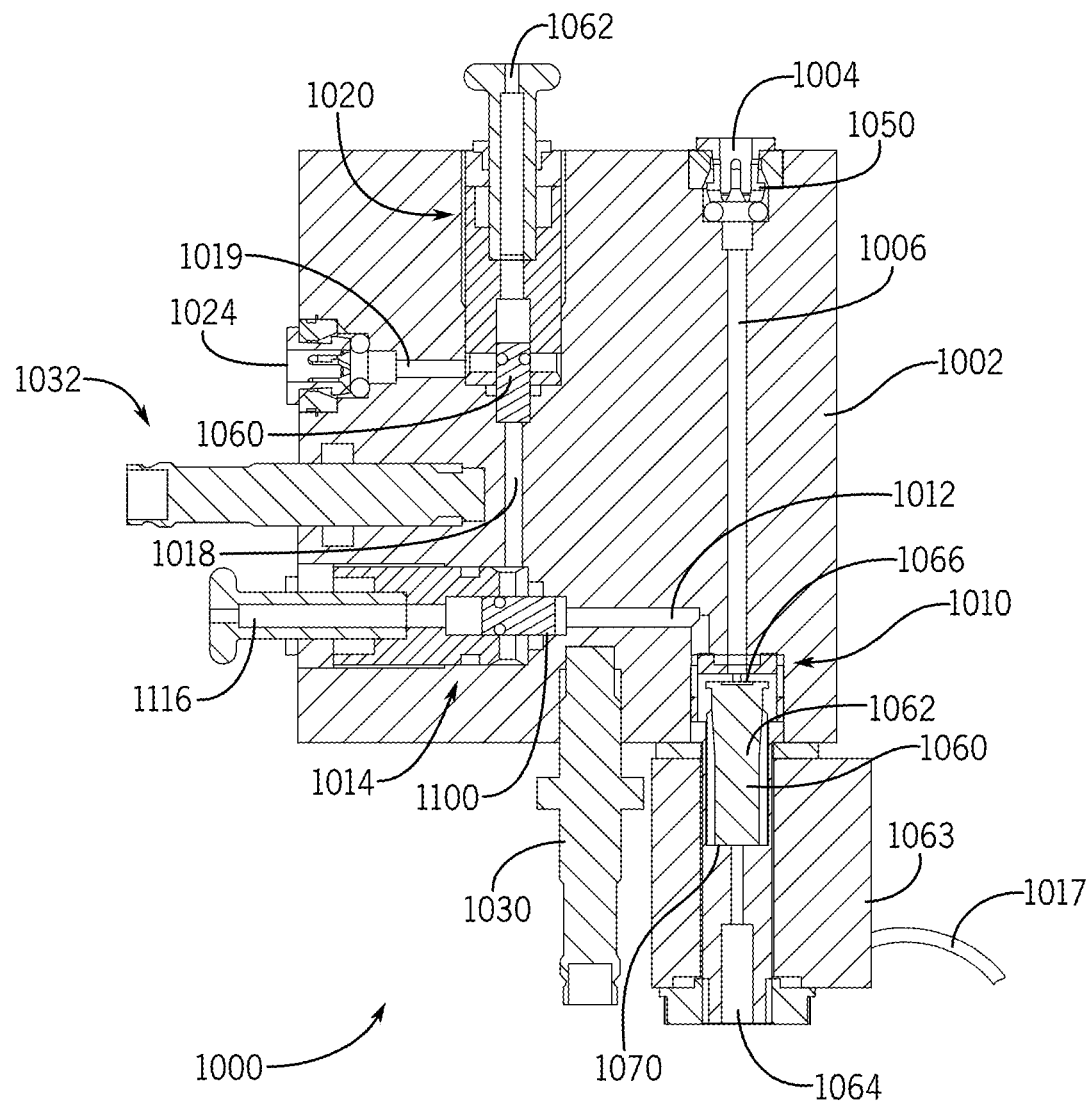
FIG. 13B is a cross sectional view of the safety valve of 13A with dip beginning to flow.
Figure 13C:
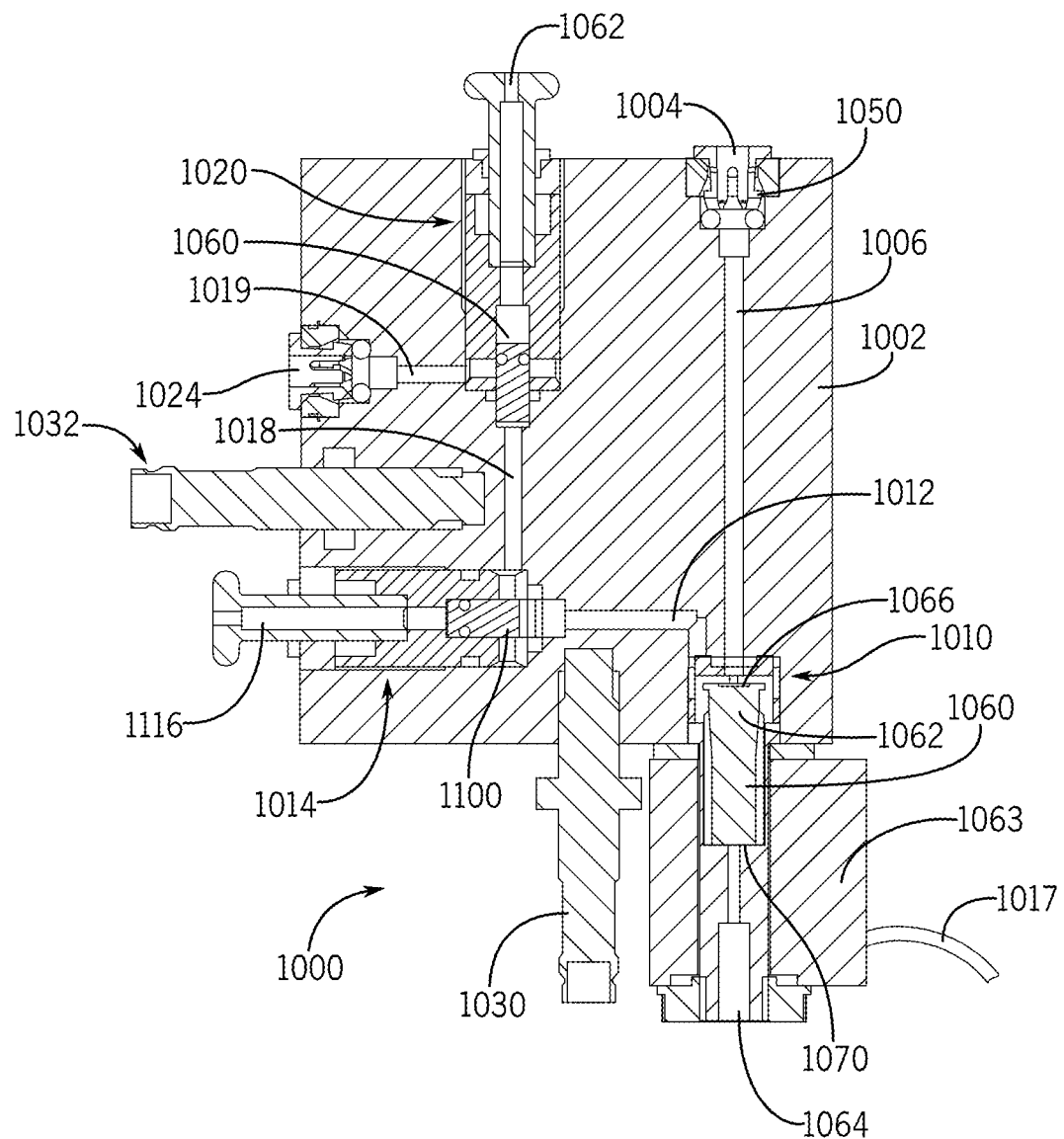
FIG. 13C is a cross sectional view of the safety valve of 13A with dip partially through the valve.
Figure 13D:
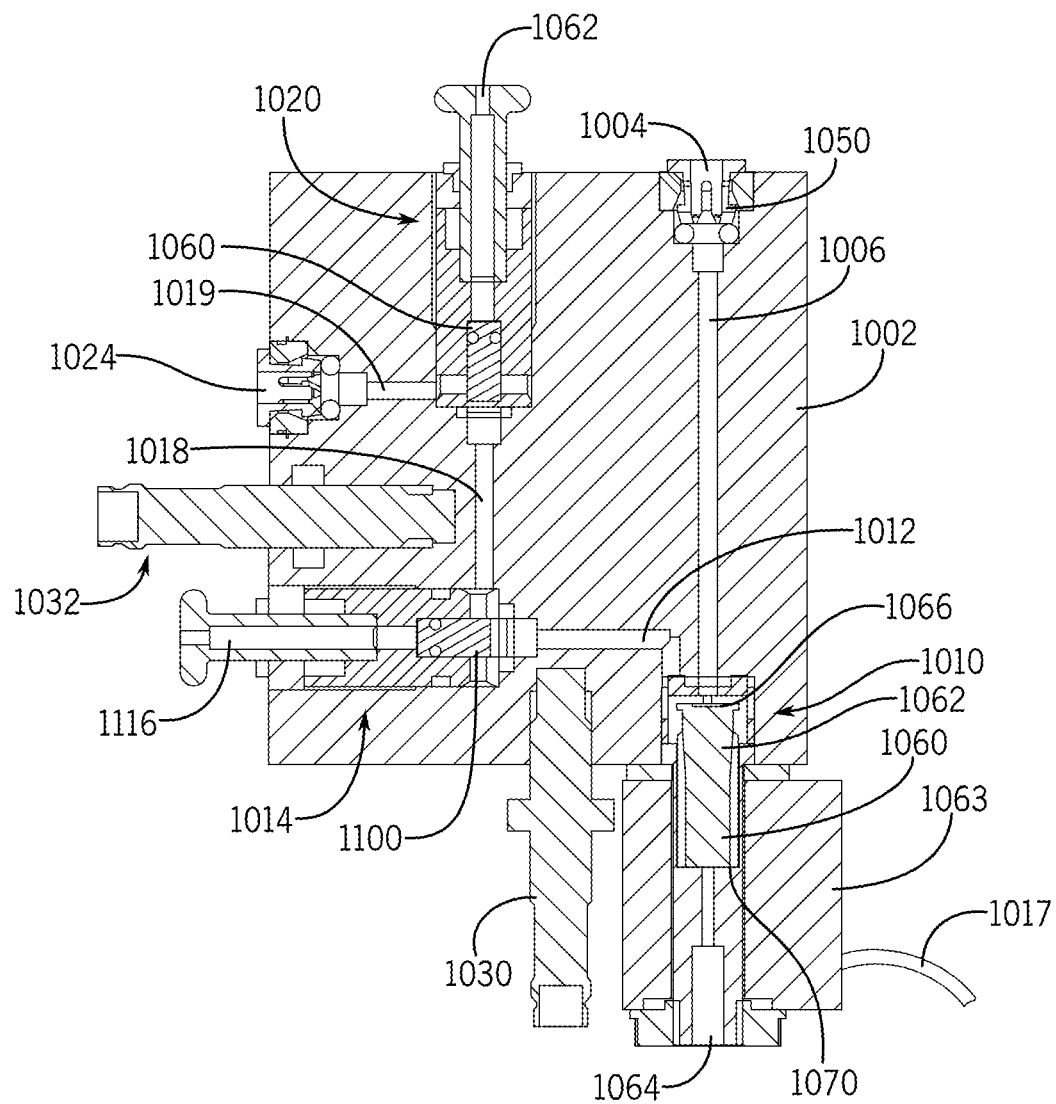
FIG. 13D is a cross sectional view of the valve of FIG. 13A open for teat dip to pass through the valve.
Figure 13E:
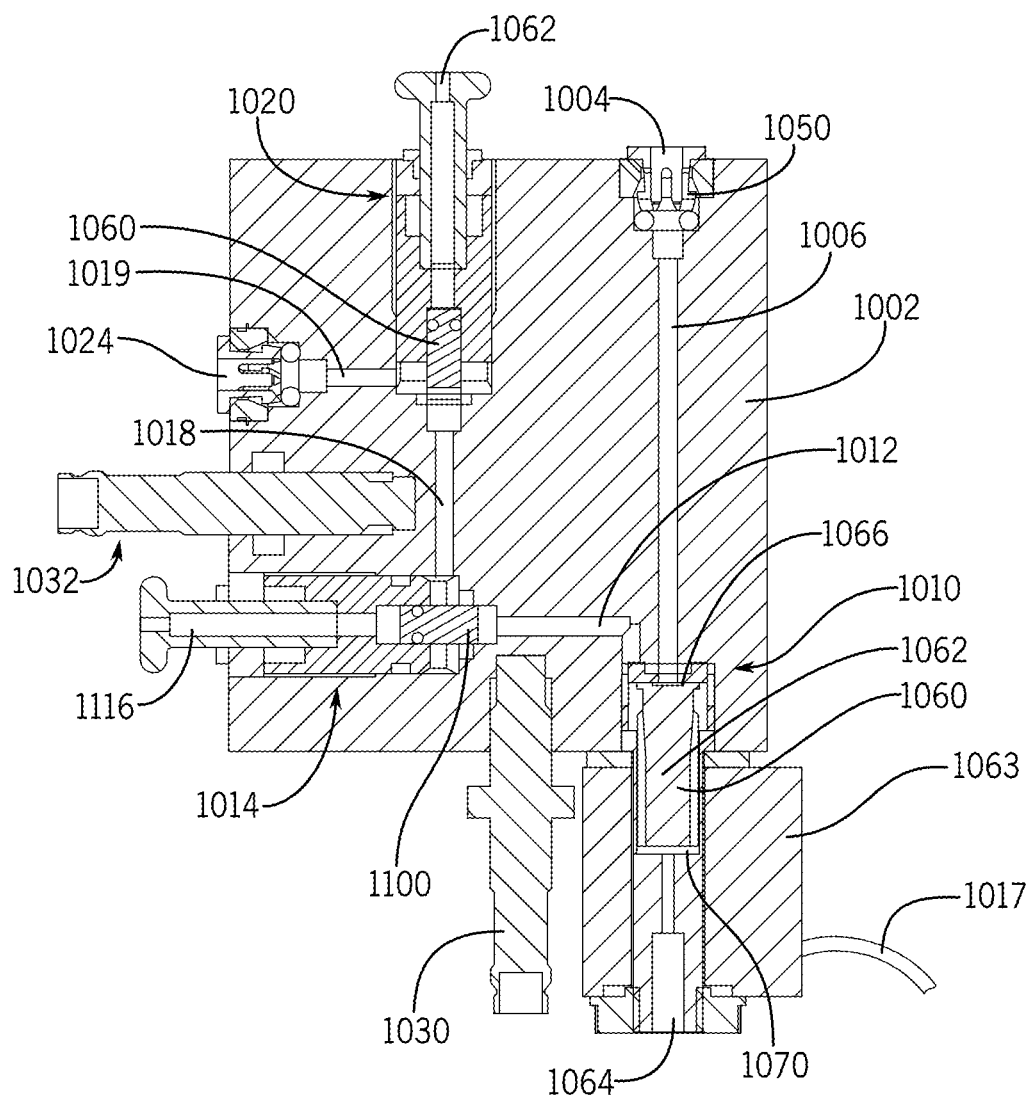
FIG. 13E is a cross sectional view of the valve of FIG. 13A partially closed after dip has flowed through the valve.

FIGS. 13A through 13E illustrate a progression of a safety valve 1000 with shuttle valves from a "Blocked (Good Milk State)" (FIG. 13A) through a "First Shuttle Valve Closing State" (FIG. 13E).

Illustrated in FIGS. 13A through 13E is a safety valve 1000 with a housing 1002, having an inlet 1004 for dairy fluids such as teat dip fluids, a bore 1006 through which the fluids flow toward an upstream valve 1010, a second bore 1012, a first shuttle valve 1014, a third bore 1018, a second shuttle valve 1020, and an outlet 1024, which can be connected to a teat dip fluid delivery line, for example. A first position sensor 1030 senses the position of the first shuttle valve 1014 and a second position sensor 1032 sense the position of the second shuttle valve 1020.

The inlet 1004 can be sized to connect to any upstream supply tube and can have a filter or other line protection device incorporated in it. The inlet also includes an appropriate coupling 1050 with a gasket for sealing the connection.

The bore 1006 can be any diameter or shape to accommodate the type of fluids that will be controlled by the safety valve 1000.

At the lower end of the bore 1006 is the first upstream valve 1010, which is essentially a 2 position-3 way valve having a plunger 1060 that is biased by a spring (not illustrated) toward a closed (upward as viewed in the figures) position. The plunger 1060 is spool-shaped and slides in a chamber 1062 in response to an actuator 1063, which is a solenoid valve in this case. The chamber 1062 has a vent 1064 beneath the plunger 1060 and a fluid outlet 1066 in fluid communication with the chamber 1062.

The vent 1064 is normally opened because the spool 1060 is normally closed. When the spool 1060 moves downward from the force of the actuator 1063, the spool 1060 contacts a seal 1070 in the bottom of the chamber 1062 to seal the vent 1064. In this position, the outlet 1066 is opened to the chamber 1062 in the area of the recessed portion of the spool 1060, which allows fluid to flow from the bore 1006, into the chamber 1062, around the spool-shaped plunger 1060, and out of the outlet 1066.

From the outlet 1066, fluid flows to the second bore 1012, which is appropriately sized and shaped, and channels the fluid to the first shuttle valve 1014, which includes a plunger 1100 that is spring-biased (spring not illustrated) to a closed position (to the right as illustrated) and will slide to the left as a result of fluid pressure in the second bore 1012. Appropriate seals are provided so that fluid cannot flow around the plunger 1100. To the left of the plunger 1100, is a vent 1116 that is open to atmosphere so there is little back pressure on the plunger 1100, so that fluid pressure can readily move the plunger to an opened position (to the left).

The position sensor 1030 senses whether the plunger 1100 is closed (all the way to the right, as illustrated) or opened. The "open" position sensed by the position sensor 1030 is not actually fully open, but regulatory requirements mandate that the sensor indicate the valve is open even before the plunger has opened a fluid flow path. Thus, the position sensor 1030 indicates an "open" valve despite the need for the plunger 1100 to move another 8 mm (0.030") before a flow path is opened.

The valve progression of the shuttle valve 1000 begins with the FIG. 13A positions of the upstream valve 1010 being closed and its corresponding vent 1064 being open. The first shuttle valve plunger 1100 is closed and it corresponding vent 1116 is open, and the second shuttle valve plunger 1160 is closed and its corresponding vent 1062 is open. This configuration results in a block-bleed-block arrangement for a safety valve 1000.

FIG. 13B illustrates the upstream valve opened with its spool 1062 is now spaced apart from the first channel 1006. Fluid flows around the spool 1062 and toward the first shuttle valve 1014, which causes the plunger 1100 to begin sliding toward an open position. Although not completely open in FIG. 13B, the position sensor 1030 will indicate that it is open to provide a margin of safety for downstream processes and components.

Once the plunger 1100 has moved even further to the left and sealed the vent 1116, the valve is in a true open position (FIG. 13C) to allow fluid to flow from the second bore 1112, through the first shuttle valve 1014, and into the third bore 1018 where it meets the second shuttle valve 1020, which is spring-biased toward a closed (downward as depicted in the figures) position and in contact with an appropriate ring seal in the third bore 1018. The plunger 1160 will move to an opened position (upward) in response to fluid pressure. The vent 1062 is open to atmosphere so that the fluid can move the plunger 1060 to an opened position by simply overcoming friction between the plunger 1160 and the seals.

The position sensor 1030 senses whether the plunger 1100 is closed (all the way to the right, as illustrated) or opened. The "open" position sensed by the position sensor 1030 is not actually fully open, but regulatory requirements mandate that the sensor indicate the valve is open even before the plunger has opened a fluid flow path. Thus, the position sensor 1030 indicates an "open" valve despite the need for the plunger 1100 to move another 8 mm (0.030") before a flow path is opened.

The second spool valve 1020 remains in its closed position because fluid pressure has not yet reached the plunger 1160.

In FIG. 13C, the upstream valve 1010 is opened and its corresponding vent (bleed) 1064 is blocked. The first shuttle valve 1014 plunger 1100 is in a true open position with its corresponding vent 1116 closed.

Fluid pressure in the third conduit 1018 has begun to open the second shuttle valve 1020 by moving the plunger 1160 toward an open position (upward). The second position sensor 1032 indicates that the plunger 1160 is open even though there remains another 8 mm (0.030") of travel for the plunger 1160 before it is truly open to allow fluid to pass.

FIG. 13D illustrates the safety valve 1000 in a fully opened position with the upstream valve 1010 fully opened and the vent (bleed) 1064 blocked, the first spool valve plunger 1100 opened and its corresponding vent 1116 is closed, and the second spool valve plunger 1160 is fully opened and its corresponding vent 1062 is closed.

FIG. 13E illustrates the process of closing the safety valve 1000, which is essentially a chain reaction process starting with closure of the upstream valve 1010, which shuts the flow of fluid through the second conduit 1012. Shutting off fluid flow (and its related fluid pressure) results in the spring-biased plunger 1100 begin to close. Fluid (and its pressure) are still present in the third conduit 1018, so the second shuttle valve plunger 1160 remains open.

Although not illustrated, when the first shuttle valve plunger 1100 closes, it cuts off fluid flow (and the related fluid pressure) in the third conduit 1018, so the second shuttle valve plunger 1160 will then begin to close as a result of its spring-bias toward a closed position. Thus, the safety valve 1000 returns to its position as seen in FIG. 13A.

As seen above in FIGS. 12A to 12C and 14A to 14C, two safety valves can be combined to process both pre-dip and post-dip, which are usually delivered through lines 67 from two separate teat dip manifolds 50 and 52. In the above embodiments, an output from a pre-dip safety valve is passed through the post-dip safety valve to avoid the use of additional check valves that would protect against cross contamination.

Also in the above embodiments, the pre-dip valve 900A and the post-dip valve 900B are either formed in the same housing or are formed in separate housings that are joined together. In the embodiment illustrated in FIGS. 15A and 15B, the pre-dip safety valves 900A and the post-dip safety valves 900B are mounted in an aligned array 913. There are four pre-dip valves 900A and four post-dip valves 900B all positioned in an array of valves 913 (see FIGS. 15A and 15B), with the pre-dip valves 900A positioned together and the post-dip valves 900B positioned together. All of the valves 900A and 900B are preferably joined to a rack 963 using hooks 965 formed or joined to the backs of each safety valve 900A, 900B, (see FIG. 16A, for example). The hooks 965 provide quick installation and maintenance for the safety valves in a robotic milker 30 (FIG. 1), for example.

When arrayed in this configuration, each pre-dip safety valve 900A is in communication with a corresponding post-dip safety valve 900B via a conduit 946. In a preferred arrangement, the first pre-dip valve 900A on the left end is in fluid communication with the first post-dip safety valve 900B, which is the fifth safety valve from the left end of the array. These two safety valves serve one of the four teat cups in a milker unit.

Next in line, the second pre-dip valve 900A from the left end is in fluid communication with the second post-dip safety valve 900B, which is the sixth safety valve from the left end of the valve array 913, and so on, so that spaced apart combinations of safety valves 900A and 900B continue through the valve array 913 resulting in four pairs of safety valves (one for each of the four teat cups) to deliver both pre-dip and post-dip to each teat cup.

Figure 16B:
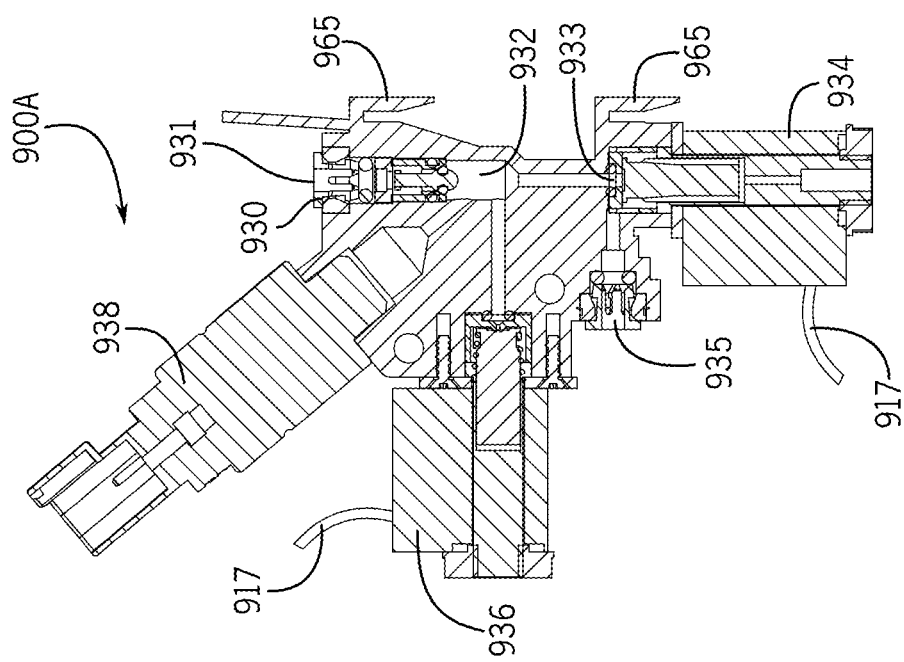
FIG. 16B is a cross sectional view of a pre-dip safety valve in a blocked position.
Figure 16A:
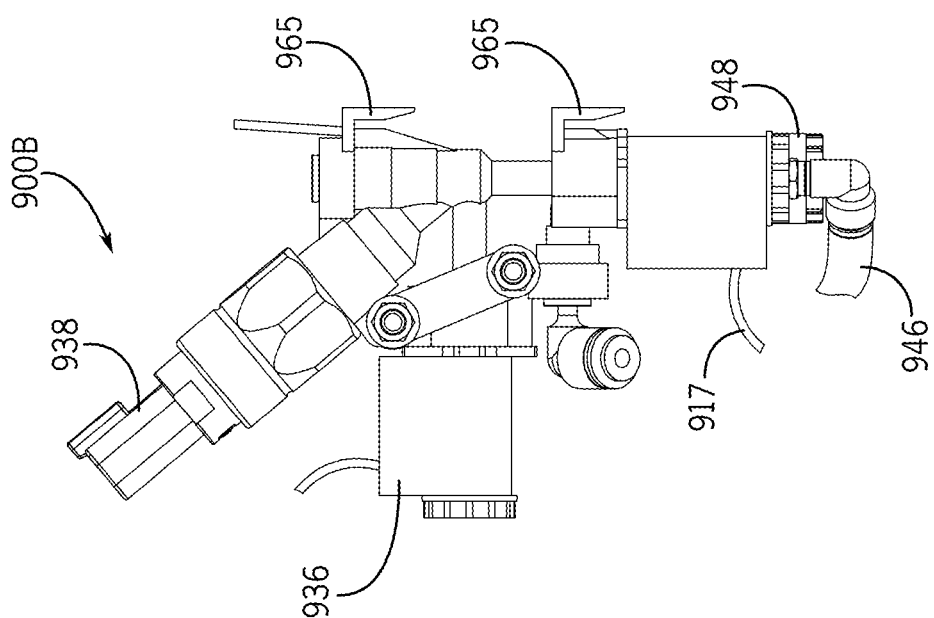
FIG. 16A is a side view of a post-dip safety valve in accordance with present invention.
Figure 16D:
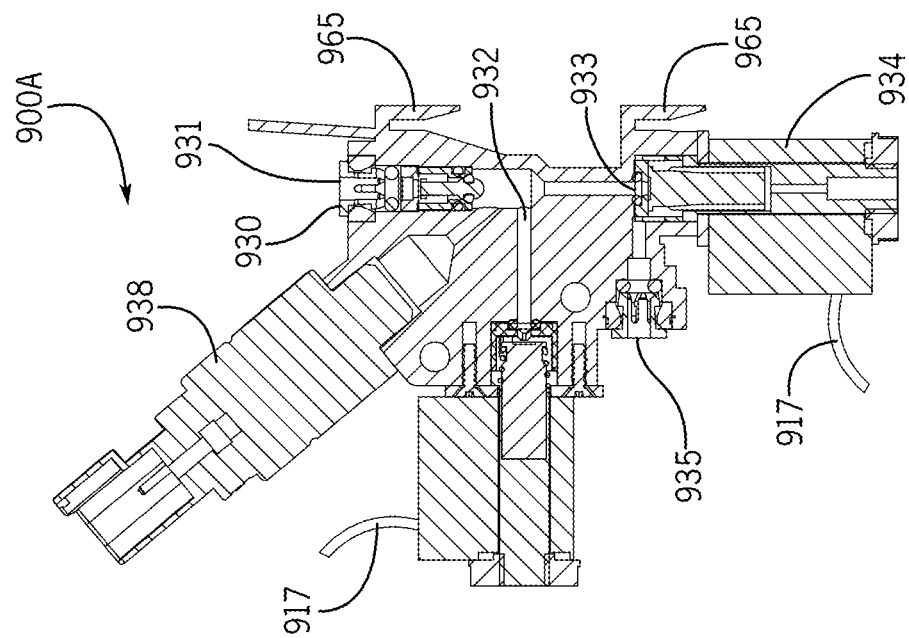
FIG. 16D is a cross sectional view of the safety valve of FIG. 16A in a pressurizing position.
Figure 16C:
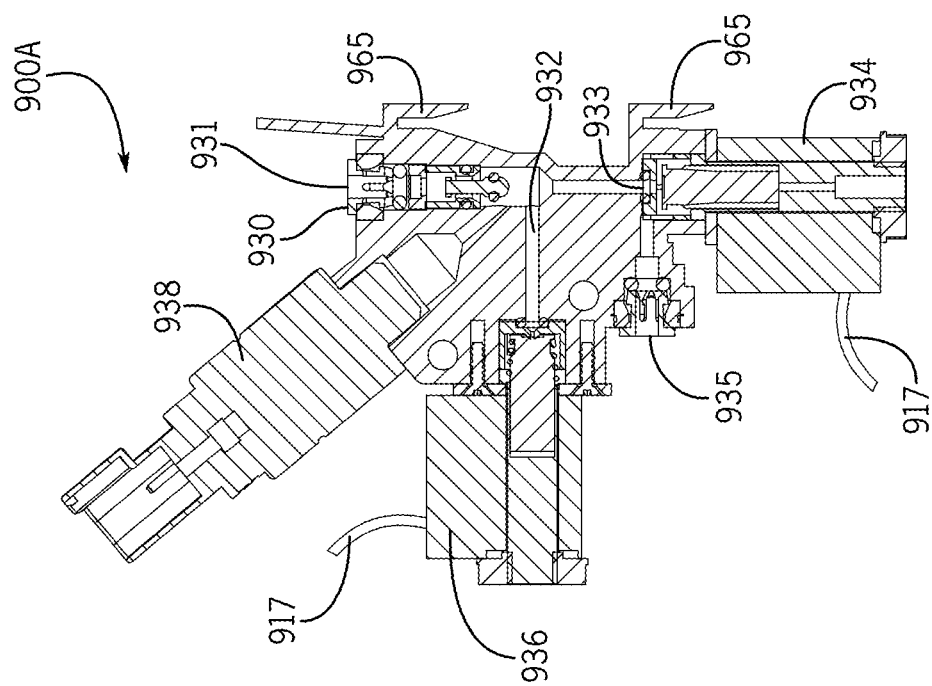
FIG. 16C is a cross sectional view of the safety valve of FIG. 16A in a dipping position.

FIG. 16A is a side view of a post-dip safety valve 900B. FIGS. 16B through 16D illustrate an example of a safety valve 900A for use in the valve array 913 is depicted. The safety valve 900A includes an upstream valve 930, a downstream valve 934 in communication with the upstream valve via a galley 932, a pressure valve 936 for pressurizing the galley 932, and a pressure sensor 938 for monitoring pressure in the galley 932. Preferably, the upstream valve 930 is a check valve and the downstream valve 934 is a 2 position-3 way valve and the pressure valve 936 is a 2 position-2 way valve, as described above. A power source 917 to power the various valves in the safety valve 900A is provided. The pre-dip fluids enter the safety valve 900A at an inlet 931 in the upstream valve 930, and exit through an outlet 935 in the downstream valve 934. A tube 946 delivers the fluid to an inlet 948 in the downstream valve 908 of the post-dip safety valve 900B and out of the outlet 961 of the downstream valve 908 of the post-dip safety valve 900B. In this arrangement, the post-dip downstream valve 908 has two inlets: a first inlet 907 for receiving post-dip when in an "opened" position and second inlet 948 for receiving pre-dip when in its "closed" position. The outlet 961 is used for both pre-dip and post-dip depending on the post-dip downstream valve 908 position.

FIG. 16B illustrates a cross section of the safety valve 900A in a blocked or milking position, with both the upstream valve 930 and the downstream valve 934 in a closed position. The pressure valve 936 is also closed to maintain pressurized gas (air) in the galley 932 for monitoring by the pressure sensor 938, and preventing contaminating fluids from passing through the safety valve 900B.

FIG. 16C illustrates the safety valve 900A in a dipping position, with the upstream valve 930 and the downstream valve 934 both open to allow teat dip to pass through. The pressure valve 936 is closed so that no pressurized gas can interfere with fluid flow through the galley 932. As described above in relation to FIGS. 12A to 12C, the pre-dip exits the safety valve 900A at the outlet 935 and passes through a conduit 946 to the corresponding post-dip safety valve 900B and its downstream valve 908 inlet 948 to then pass through to an outlet 961 to be delivered to the teat cup in delivery line 68.

In the case of a post-dip safety valve 900B in an "open" dipping position, the post-dip simply passes through the first inlet 907 of the downstream valve 908 and through the common outlet 961 to be delivered to the teat cup in line 68.

FIG. 16D illustrates the safety valve 900A in a pressurizing position with the upstream valve 930 and the downstream valve 934 both closed, but the pressure valve 936 is open to allow pressurized gas into the galley 932 to prevent contaminating fluids from passing through the valve 900A and where the pressure levels can be monitored by the pressure sensor 938 to determine whether the valve 900A has leaks or is otherwise in need of maintenance or replacement.

The foregoing detailed description is included for clearness of understanding only, and no unnecessary limitations therefrom should be read into the following claims.

The invention claimed is:

1. A teat dip applicator valve assembly comprising:
a teat dip fluid conduit defining a flow path having a first end and a second end;
a first valve at the first end of the flow path and having an open position and a closed position;
a second valve at the second end of the flow path and having an open position and a closed position;
a pressurized fluid source in fluid communication with the flow path when the first valve is in the closed position and the second valve is in the closed position; and
a pressure monitor in communication with the flow path to determine fluid pressure in the flow path.

2. The teat dip applicator valve assembly of claim 1, wherein the pressure monitor is set to react to a predetermined fluid pressure.

3. The teat dip applicator valve assembly of claim 1, wherein the pressure monitor generates data corresponding to fluid pressure in the flow path, and the valve assembly further comprises:
a controller that compares the data to a predetermined flow channel pressure range and generates a signal if the data comparison indicates that the data is outside of the predetermined range.

4. The teat dip applicator valve assembly of claim 1, wherein the first valve is a two-position, three-way valve.

5. The teat dip applicator valve assembly of claim 1, wherein the second valve is a two-position, three-way valve.

6. The teat dip applicator valve assembly of claim 1, wherein the first valve is a shuttle valve.

7. The teat dip applicator valve assembly of claim 1, wherein the second valve is a shuttle valve.

8. The teat dip applicator valve assembly of claim 1, wherein the pressurized fluid source communicates pressurized gas to the flow channel when the first valve is in the closed position and the second valve is in the closed position.

9. The teat dip applicator valve assembly of claim 1, wherein the flow channel is open when the first valve is in the open position and the second valve is in the open position.

10. The teat dip applicator valve assembly of claim 1, wherein the flow channel receives fluid through the first valve and emits fluid through the second valve.

11. The teat dip applicator valve assembly of claim 1, wherein the first valve is an upstream valve.

12. The teat dip applicator valve assembly of claim 1, wherein the second valve is a downstream valve.

13. The teat dip applicator valve assembly of claim 1, and further comprising:
a control valve upstream from the first valve, and the control valve has an open position and a closed position.

14. A teat dip applicator safety valve assembly comprising:
a pre-dip safety valve having:
a pre-dip upstream valve having a pre-dip fluid inlet and an outlet, and having an open position and a closed position;
a pre-dip fluid galley in communication with the pre-dip upstream valve outlet, and having an open position and a closed position;
a pre-dip downstream valve having an inlet in communication with the galley and a pre-dip outlet, and having an open position and a closed position;
a post-dip safety valve having:
a post-dip upstream valve having a post-dip fluid inlet and an outlet, and having an open position and a closed position;
a post-dip fluid galley in communication with the post-dip upstream valve outlet, and having an open position and a closed position;
a post-dip downstream valve having a post-dip inlet in communication with the post-dip galley, and having an open position and a closed position; a pre-dip inlet in communication with the pre-dip outlet of the pre-dip downstream valve; and a common outlet in communication with the post-dip inlet when the post-dip downstream valve is in the closed position and the pre-dip inlet when the post-dip downstream valve is in the open position.

15. The teat dip applicator safety valve assembly of claim 14, and further comprising:
a pressure valve having an open position in communication with the pre-dip fluid galley and a source of pressurized gas, and a closed position to close the pre-dip galley from the source of pressurized gas.

16. The teat dip applicator safety valve assembly of claim 14, and further comprising:
a pressure valve having an open position in communication with the pre-dip fluid galley and a source of pressurized gas, and a closed position to close the pre-dip galley from the source of pressurized gas; and
a pressure sensor in communication with the pre-dip galley to monitor pressure in the pre-dip galley.

17. The teat dip applicator safety valve assembly of claim 14, and further comprising:
a pressure valve having an open position in communication with the post-dip fluid galley and a source of pressurized gas, and a closed position to close the post-dip galley from the source of pressurized gas.

18. The teat dip applicator safety valve assembly of claim 14, and further comprising:

a pressure valve having an open position in communication with the post-dip fluid galley and a source of pressurized gas, and a closed position to close the post-dip galley from the source of pressurized gas; and a pressure sensor in communication with the post-dip galley to monitor pressure in the post-dip galley.

19. The teat dip applicator safety valve assembly of claim 14, and further comprising:

a pressure valve having an open position in communication with the pre-dip fluid galley and a source of pressurized gas, and a closed position to close the pre-dip galley from the source of pressurized gas;

a pressure sensor in communication with the pre-dip galley to monitor pressure in the pre-dip galley;

a pressure valve having an open position in communication with the post-dip fluid galley and a source of pressurized gas, and a closed position to close the post-dip galley from the source of pressurized gas; and a pressure sensor in communication with the post-dip galley to monitor pressure in the post-dip galley.

20. The teat dip applicator safety valve assembly of claim 14, and further comprising:

a pre-dip conduit in communication between the pre-dip downstream valve outlet and the post-dip downstream valve pre-dip inlet.

* * * * *